United States Patent
Leach et al.

(10) Patent No.: US 8,992,862 B2
(45) Date of Patent: Mar. 31, 2015

(54) ALL-IN-ONE MEANS OF SEPARATING BLOOD COMPONENTS

(71) Applicant: Biomet Biologics, LLC, Warsaw, IN (US)

(72) Inventors: Michael D. Leach, Warsaw, IN (US); Jason Chavarria, Warsaw, IN (US)

(73) Assignee: Biomet Biologics, LLC, Warsaw, IN (US)

(*) Notice: Subject to any disclaimer, the term of this patent is extended or adjusted under 35 U.S.C. 154(b) by 14 days.

(21) Appl. No.: 13/677,897

(22) Filed: Nov. 15, 2012

(65) Prior Publication Data

US 2013/0068676 A1 Mar. 21, 2013

Related U.S. Application Data

(62) Division of application No. 12/417,789, filed on Apr. 3, 2009, now Pat. No. 8,313,954.

(51) Int. Cl.
  *B01D 17/12* (2006.01)
  *A61M 1/02* (2006.01)
  (Continued)

(52) U.S. Cl.
  CPC ............... *B01D 17/12* (2013.01); *A61M 1/029* (2013.01); *A61M 2202/0415* (2013.01);
  (Continued)

(58) Field of Classification Search
  CPC . B01L 3/5021; B01L 3/50215; G01N 33/491; G01N 33/5002
  USPC ......... 422/533, 548, 559, 918, 914, 547, 549, 422/527
  See application file for complete search history.

(56) References Cited

U.S. PATENT DOCUMENTS

| 280,820 A | 7/1883 | Hickson et al. |
| 593,333 A | 11/1897 | Park |

(Continued)

FOREIGN PATENT DOCUMENTS

| AU | 696278 | 1/1999 |
| BR | 9103724 | 3/1993 |

(Continued)

OTHER PUBLICATIONS

International Preliminary Report on Patentability and Written Opinion mailed Oct. 31, 2013 for PCT/US2012/034104 claiming benefit of U.S. Appl. No. 13/089,591, filed Apr. 19, 2011.

(Continued)

*Primary Examiner* — Brian R Gordon
(74) *Attorney, Agent, or Firm* — Harness, Dickey

(57) ABSTRACT

A separation device including a first buoy, a second buoy, a first valve, and a second valve. The first buoy is mounted to a buoy guide post and slidably mounted within a separation chamber. The second buoy is slidably mounted to the guide post and movable between a first position and a second position. The second buoy closes the first valve and opens the second valve when in the first position. The second buoy opens the first valve and closes the second valve when in the second position. The second buoy has a density such that after spinning the device for a suitable period of time a first component of the composition is isolated between the first buoy and the second buoy and a second component of the composition is isolated between the second buoy and the end of the separation chamber that is opposite to a port.

20 Claims, 10 Drawing Sheets

(51) Int. Cl.
*G01N 33/49* (2006.01)
*B01L 3/02* (2006.01)
*B01L 3/00* (2006.01)

(52) U.S. Cl.
CPC ............ *A61M 2202/0427* (2013.01); *A61M 2202/0429* (2013.01); *A61M 2202/0464* (2013.01); *A61M 2202/10* (2013.01); *B01L 3/0217* (2013.01); *B01L 3/50215* (2013.01); *B01L 2400/0409* (2013.01); *G01N 33/491* (2013.01)
USPC ............ 422/533; 422/527; 422/548; 422/549

(56) References Cited

U.S. PATENT DOCUMENTS

| | | |
|---|---|---|
| 1,468,313 A | 9/1923 | Lux |
| 1,593,814 A | 7/1926 | Vogel |
| 2,722,257 A | 11/1955 | Lockhart |
| 3,013,557 A | 12/1961 | Pallotta |
| 3,141,846 A | 7/1964 | Laven, Jr. |
| 3,159,159 A | 12/1964 | Cohen |
| 3,300,051 A | 1/1967 | Mitchell |
| 3,409,165 A | 11/1968 | Creith |
| 3,420,374 A | 1/1969 | Umeda |
| 3,441,143 A | 4/1969 | Kudlaty |
| 3,453,364 A | 7/1969 | Flodin et al. |
| 3,469,369 A | 9/1969 | Helmke |
| 3,508,653 A | 4/1970 | Coleman |
| 3,545,671 A | 12/1970 | Ross |
| 3,583,627 A | 6/1971 | Wilson |
| 3,596,652 A | 8/1971 | Winkelman |
| 3,647,070 A | 3/1972 | Adler |
| 3,654,925 A | 4/1972 | Holderith |
| 3,661,265 A | 5/1972 | Greenspan |
| 3,706,305 A | 12/1972 | Berger et al. |
| 3,706,306 A | 12/1972 | Berger et al. |
| 3,723,244 A | 3/1973 | Breillatt, Jr. |
| 3,741,400 A | 6/1973 | Dick |
| 3,779,383 A | 12/1973 | Ayres |
| 3,785,549 A | 1/1974 | Latham, Jr. |
| 3,814,248 A | 6/1974 | Lawhead |
| 3,849,072 A | 11/1974 | Ayres |
| 3,850,369 A | 11/1974 | Bull et al. |
| 3,879,295 A | 4/1975 | Glover et al. |
| 3,887,466 A | 6/1975 | Ayres |
| 3,894,952 A | 7/1975 | Ayres |
| 3,896,733 A | 7/1975 | Rosenberg |
| 3,897,337 A | 7/1975 | Ayres |
| 3,897,343 A | 7/1975 | Ayres |
| 3,909,419 A | 9/1975 | Ayres |
| 3,929,646 A | 12/1975 | Adler |
| 3,931,010 A | 1/1976 | Ayres et al. |
| 3,931,018 A | 1/1976 | North, Jr. |
| 3,935,113 A | 1/1976 | Ayres |
| 3,937,211 A | 2/1976 | Merten |
| 3,941,699 A | 3/1976 | Ayres |
| 3,945,928 A | 3/1976 | Ayres |
| 3,951,801 A | 4/1976 | Ayres |
| 3,957,654 A | 5/1976 | Ayres |
| 3,962,085 A | 6/1976 | Liston et al. |
| 3,965,889 A | 6/1976 | Sachs |
| 3,972,812 A | 8/1976 | Gresl, Jr. |
| 3,982,691 A | 9/1976 | Schlutz |
| 4,001,122 A | 1/1977 | Griffin |
| 4,020,831 A | 5/1977 | Adler |
| 4,046,699 A | 9/1977 | Zine, Jr. |
| 4,055,501 A | 10/1977 | Cornell |
| 4,059,108 A | 11/1977 | Latham, Jr. |
| 4,066,549 A | 1/1978 | Oeser et al. |
| 4,077,396 A | 3/1978 | Wardlaw et al. |
| 4,088,582 A | 5/1978 | Murty et al. |
| 4,146,172 A | 3/1979 | Cullis et al. |
| 4,152,270 A | 5/1979 | Cornell |
| 4,154,690 A | 5/1979 | Ballies |
| 4,159,896 A | 7/1979 | Levine et al. |
| 4,187,979 A | 2/1980 | Cullis et al. |
| 4,189,385 A | 2/1980 | Greenspan |
| 4,203,840 A | 5/1980 | Stoeppler et al. |
| 4,204,537 A | 5/1980 | Latham, Jr. |
| 4,225,580 A | 9/1980 | Rothman et al. |
| 4,229,298 A | 10/1980 | Bange |
| 4,269,718 A | 5/1981 | Persidsky |
| 4,294,707 A | 10/1981 | Ikeda et al. |
| 4,298,598 A | 11/1981 | Schwarz et al. |
| 4,300,717 A | 11/1981 | Latham, Jr. |
| 4,303,193 A | 12/1981 | Latham, Jr. |
| 4,314,823 A | 2/1982 | Rich, Jr. et al. |
| 4,322,298 A | 3/1982 | Persidsky |
| 4,332,351 A | 6/1982 | Kellogg et al. |
| 4,362,567 A | 12/1982 | Schwarz et al. |
| 4,364,832 A | 12/1982 | Ballies |
| 4,377,572 A | 3/1983 | Schwarz et al. |
| 4,379,849 A | 4/1983 | Heimreid |
| 4,411,794 A | 10/1983 | Schwinn et al. |
| 4,414,976 A | 11/1983 | Schwarz et al. |
| 4,416,654 A | 11/1983 | Schoendorfer et al. |
| 4,417,981 A | 11/1983 | Nugent |
| 4,424,132 A | 1/1984 | Iriguchi et al. |
| 4,427,650 A | 1/1984 | Stroetmann et al. |
| 4,427,651 A | 1/1984 | Stroetmann et al. |
| 4,442,655 A | 4/1984 | Stroetmann et al. |
| 4,443,345 A | 4/1984 | Wells |
| 4,445,550 A | 5/1984 | Davis et al. |
| 4,446,021 A | 5/1984 | Aufderhaar et al. |
| 4,453,927 A | 6/1984 | Sinko |
| 4,453,939 A | 6/1984 | Zimmerman et al. |
| 4,464,167 A | 8/1984 | Schoendorfer et al. |
| 4,511,662 A | 4/1985 | Baran et al. |
| 4,537,767 A | 8/1985 | Rothman et al. |
| RE32,089 E | 3/1986 | Blatt et al. |
| 4,577,514 A | 3/1986 | Bradley et al. |
| 4,610,656 A | 9/1986 | Mortensen |
| 4,617,009 A | 10/1986 | Ohlin et al. |
| 4,627,879 A | 12/1986 | Rose et al. |
| 4,631,055 A | 12/1986 | Redl et al. |
| 4,632,761 A | 12/1986 | Bowers et al. |
| 4,639,316 A | 1/1987 | Eldegheidy |
| 4,650,678 A | 3/1987 | Fuhge et al. |
| 4,655,211 A | 4/1987 | Sakamoto et al. |
| 4,672,969 A | 6/1987 | Dew |
| 4,675,117 A | 6/1987 | Neumann et al. |
| 4,680,025 A | 7/1987 | Kruger et al. |
| 4,714,457 A | 12/1987 | Alterbaum |
| 4,722,790 A | 2/1988 | Cawley et al. |
| 4,724,317 A | 2/1988 | Brown et al. |
| 4,735,616 A | 4/1988 | Eibl et al. |
| 4,735,726 A | 4/1988 | Duggins |
| 4,738,655 A | 4/1988 | Brimhall et al. |
| 4,755,300 A | 7/1988 | Fischel et al. |
| 4,755,301 A | 7/1988 | Bowers |
| 4,770,779 A | 9/1988 | Ichikawa et al. |
| 4,776,964 A | 10/1988 | Schoendorfer et al. |
| 4,818,291 A | 4/1989 | Iwatsuki et al. |
| 4,818,386 A | 4/1989 | Burns |
| 4,828,710 A | 5/1989 | Itoh et al. |
| 4,832,851 A | 5/1989 | Bowers et al. |
| 4,834,890 A | 5/1989 | Brown et al. |
| 4,839,058 A | 6/1989 | Cawley et al. |
| 4,844,818 A | 7/1989 | Smith |
| 4,846,780 A | 7/1989 | Galloway et al. |
| 4,846,835 A | 7/1989 | Grande |
| 4,850,952 A | 7/1989 | Figdor et al. |
| 4,853,137 A | 8/1989 | Ersson et al. |
| 4,871,462 A | 10/1989 | Fischel et al. |
| 4,874,368 A | 10/1989 | Miller et al. |
| 4,877,520 A | 10/1989 | Burns |
| 4,879,031 A | 11/1989 | Panzani et al. |
| 4,900,453 A | 2/1990 | Sedlmayer |
| 4,902,281 A | 2/1990 | Avoy |
| 4,909,251 A | 3/1990 | Seelich et al. |
| 4,915,847 A | 4/1990 | Dillon et al. |
| 4,917,801 A | 4/1990 | Luderer et al. |
| 4,928,603 A | 5/1990 | Rose et al. |

(56) References Cited

U.S. PATENT DOCUMENTS

| | | |
|---|---|---|
| 4,929,242 A | 5/1990 | Desecki et al. |
| 4,933,291 A | 6/1990 | Daiss et al. |
| 4,939,081 A | 7/1990 | Figdor et al. |
| 4,943,273 A | 7/1990 | Pages et al. |
| 4,946,601 A | 8/1990 | Fiehler |
| 4,950,220 A | 8/1990 | Wells et al. |
| 4,957,637 A | 9/1990 | Cornell |
| 4,957,638 A | 9/1990 | Smith |
| 4,973,168 A | 11/1990 | Chan |
| 4,983,157 A | 1/1991 | Pober et al. |
| 4,983,158 A | 1/1991 | Headley |
| 4,985,153 A | 1/1991 | Kuroda et al. |
| 5,000,970 A | 3/1991 | Shanbhag et al. |
| 5,002,571 A | 3/1991 | O'Donnell, Jr. et al. |
| 5,019,243 A | 5/1991 | McEwen et al. |
| 5,024,613 A | 6/1991 | Vasconcellos et al. |
| 5,030,215 A | 7/1991 | Morse et al. |
| 5,030,341 A | 7/1991 | McEwen et al. |
| 5,039,401 A | 8/1991 | Columbus et al. |
| 5,045,048 A | 9/1991 | Kaleskas et al. |
| 5,047,004 A | 9/1991 | Wells |
| 5,053,127 A | 10/1991 | Schoendorfer et al. |
| 5,053,134 A | 10/1991 | Luderer et al. |
| 5,071,570 A | 12/1991 | Shiraki et al. |
| 5,080,262 A | 1/1992 | Herold et al. |
| 5,086,784 A | 2/1992 | Levine et al. |
| 5,100,564 A | 3/1992 | Pall et al. |
| 5,104,375 A | 4/1992 | Wolf et al. |
| 5,112,484 A | 5/1992 | Zuk, Jr. |
| 5,112,490 A | 5/1992 | Turpen |
| 5,131,907 A | 7/1992 | Williams et al. |
| 5,137,832 A | 8/1992 | Levine et al. |
| 5,141,645 A | 8/1992 | Shiraki et al. |
| 5,147,290 A | 9/1992 | Jonsson |
| 5,152,905 A | 10/1992 | Pall et al. |
| 5,156,613 A | 10/1992 | Sawyer |
| 5,165,938 A | 11/1992 | Knighton |
| 5,171,456 A | 12/1992 | Hwang et al. |
| 5,173,295 A | 12/1992 | Wehling et al. |
| 5,178,602 A | 1/1993 | Wells |
| 5,185,001 A | 2/1993 | Galanakis |
| 5,188,583 A | 2/1993 | Guigan et al. |
| 5,190,057 A | 3/1993 | Sarfarazi |
| 5,190,759 A | 3/1993 | Lindblad et al. |
| 5,197,985 A | 3/1993 | Caplan et al. |
| 5,203,825 A | 4/1993 | Haynes et al. |
| 5,204,537 A | 4/1993 | Bennet et al. |
| 5,206,023 A | 4/1993 | Hunziker et al. |
| 5,207,638 A | 5/1993 | Choksi et al. |
| 5,217,426 A | 6/1993 | Bacehowski et al. |
| 5,217,627 A | 6/1993 | Pall et al. |
| 5,219,328 A | 6/1993 | Morse et al. |
| 5,226,877 A | 7/1993 | Epstein |
| 5,226,914 A | 7/1993 | Caplan et al. |
| 5,234,608 A | 8/1993 | Duff |
| 5,236,604 A | 8/1993 | Fiehler |
| 5,251,786 A | 10/1993 | Sarrine |
| 5,258,126 A | 11/1993 | Pall et al. |
| 5,260,420 A | 11/1993 | Burnouf-Radosevich et al. |
| 5,269,927 A | 12/1993 | Fiehler |
| 5,271,852 A | 12/1993 | Luoma, II |
| 5,279,825 A | 1/1994 | Wehling et al. |
| 5,281,342 A | 1/1994 | Biesel et al. |
| 5,290,552 A | 3/1994 | Sierra et al. |
| 5,290,918 A | 3/1994 | Bui-Khac et al. |
| 5,298,171 A | 3/1994 | Biesel et al. |
| 5,304,372 A | 4/1994 | Michalski et al. |
| 5,316,674 A | 5/1994 | Pall et al. |
| 5,318,524 A | 6/1994 | Morse et al. |
| 5,318,782 A | 6/1994 | Weis-Fogh et al. |
| 5,321,126 A | 6/1994 | van Dommelen et al. |
| 5,322,620 A | 6/1994 | Brown et al. |
| 5,330,974 A | 7/1994 | Pines et al. |
| 5,344,752 A | 9/1994 | Murphy |
| 5,354,483 A | 10/1994 | Furse |
| 5,370,221 A | 12/1994 | Magnusson et al. |
| 5,370,802 A | 12/1994 | Brown |
| 5,372,945 A | 12/1994 | Alchas et al. |
| 5,376,263 A | 12/1994 | Fischel |
| 5,387,187 A | 2/1995 | Fell et al. |
| 5,393,674 A | 2/1995 | Levine et al. |
| 5,395,923 A | 3/1995 | Bui-Khac et al. |
| 5,403,272 A | 4/1995 | Deniega et al. |
| 5,405,607 A | 4/1995 | Epstein |
| 5,409,833 A | 4/1995 | Hu et al. |
| 5,411,885 A | 5/1995 | Marx |
| 5,417,650 A | 5/1995 | Gordon |
| 5,420,250 A | 5/1995 | Lontz |
| 5,443,481 A | 8/1995 | Lee |
| 5,454,958 A | 10/1995 | Fiehler |
| 5,456,693 A | 10/1995 | Conston et al. |
| 5,456,885 A | 10/1995 | Coleman et al. |
| 5,474,687 A | 12/1995 | Van Vlasselaer |
| 5,480,378 A | 1/1996 | Weis-Fogh et al. |
| 5,484,383 A | 1/1996 | Fitch, Jr. et al. |
| 5,486,359 A | 1/1996 | Caplan et al. |
| 5,494,578 A | 2/1996 | Brown et al. |
| 5,494,592 A | 2/1996 | Latham, Jr. et al. |
| 5,501,371 A | 3/1996 | Schwartz-Feldman |
| 5,505,685 A | 4/1996 | Antwiler |
| 5,510,102 A | 4/1996 | Cochrum |
| 5,520,885 A | 5/1996 | Coelho et al. |
| 5,525,477 A | 6/1996 | Hassouna |
| 5,533,518 A | 7/1996 | Vogler |
| 5,560,830 A | 10/1996 | Coleman et al. |
| 5,575,778 A | 11/1996 | Hardt et al. |
| 5,577,513 A | 11/1996 | Van Vlasselaer |
| 5,585,007 A | 12/1996 | Antanavich et al. |
| 5,588,958 A | 12/1996 | Cunningham et al. |
| 5,589,462 A | 12/1996 | Patat et al. |
| 5,601,711 A | 2/1997 | Sklar et al. |
| 5,601,727 A | 2/1997 | Bormann et al. |
| 5,603,845 A | 2/1997 | Holm |
| 5,607,579 A | 3/1997 | Latham, Jr. et al. |
| 5,614,106 A | 3/1997 | Payrat et al. |
| 5,618,663 A | 4/1997 | Delmas et al. |
| 5,632,895 A | 5/1997 | Tsukagoshi et al. |
| 5,632,905 A | 5/1997 | Haynes |
| 5,641,414 A | 6/1997 | Brown |
| 5,641,622 A | 6/1997 | Lake et al. |
| 5,643,192 A | 7/1997 | Hirsh et al. |
| 5,643,193 A | 7/1997 | Papillon et al. |
| 5,645,540 A | 7/1997 | Henniges et al. |
| 5,646,004 A | 7/1997 | Van Vlasselaer |
| 5,648,223 A | 7/1997 | Van Vlasselaer |
| 5,649,903 A | 7/1997 | Deniega et al. |
| 5,663,051 A | 9/1997 | Vlasselaer |
| 5,674,173 A | 10/1997 | Hlavinka et al. |
| 5,707,331 A | 1/1998 | Wells et al. |
| 5,707,647 A | 1/1998 | Dunn et al. |
| 5,707,876 A | 1/1998 | Levine |
| 5,716,616 A | 2/1998 | Prockop et al. |
| 5,723,331 A | 3/1998 | Tubo et al. |
| 5,724,988 A | 3/1998 | Dennehey et al. |
| 5,733,466 A | 3/1998 | Benebo et al. |
| 5,733,545 A | 3/1998 | Hood, III |
| 5,736,033 A | 4/1998 | Coleman et al. |
| 5,738,784 A | 4/1998 | Holm et al. |
| 5,738,796 A | 4/1998 | Bormann et al. |
| 5,750,025 A | 5/1998 | Holmes et al. |
| 5,750,658 A | 5/1998 | Coelho et al. |
| 5,762,798 A | 6/1998 | Wenthold et al. |
| 5,785,700 A | 7/1998 | Olson |
| 5,786,217 A | 7/1998 | Tubo et al. |
| 5,788,662 A | 8/1998 | Antanavich et al. |
| 5,792,344 A | 8/1998 | Holm |
| 5,795,489 A | 8/1998 | Holm et al. |
| 5,795,571 A | 8/1998 | Cederholm-Williams et al. |
| 5,795,751 A | 8/1998 | Apel |
| 5,811,094 A | 9/1998 | Caplan et al. |
| 5,811,151 A | 9/1998 | Hendriks et al. |
| 5,817,519 A | 10/1998 | Zelmanovic et al. |
| 5,823,986 A | 10/1998 | Peterson |
| 5,824,084 A | 10/1998 | Muschler |

(56) References Cited

U.S. PATENT DOCUMENTS

| | | |
|---|---|---|
| 5,830,359 A | 11/1998 | Knight et al. |
| 5,833,866 A | 11/1998 | Brown |
| 5,834,418 A | 11/1998 | Brazeau et al. |
| 5,837,150 A | 11/1998 | Langley et al. |
| 5,840,502 A | 11/1998 | Van Vlasselaer |
| 5,853,600 A | 12/1998 | McNeal et al. |
| 5,860,937 A | 1/1999 | Cohen |
| 5,863,892 A | 1/1999 | Stern et al. |
| 5,865,785 A | 2/1999 | Bischof |
| 5,885,239 A | 3/1999 | Headley et al. |
| 5,889,584 A | 3/1999 | Wardlaw |
| 5,895,346 A | 4/1999 | Wells et al. |
| 5,899,874 A | 5/1999 | Jonsson et al. |
| 5,900,245 A | 5/1999 | Sawhney et al. |
| 5,906,934 A | 5/1999 | Grande et al. |
| 5,916,557 A | 6/1999 | Berlowitz-Tarrant et al. |
| 5,916,743 A | 6/1999 | Lake et al. |
| 5,918,622 A | 7/1999 | Perez et al. |
| 5,924,972 A | 7/1999 | Turvaville et al. |
| 5,934,803 A | 8/1999 | Hutter |
| 5,938,621 A | 8/1999 | Kelly et al. |
| 5,951,160 A | 9/1999 | Ronk |
| 5,955,032 A | 9/1999 | Kelly et al. |
| 5,955,436 A | 9/1999 | Kunkle, Jr. |
| 5,958,250 A | 9/1999 | Brown et al. |
| 5,958,253 A | 9/1999 | Holm et al. |
| 5,961,210 A | 10/1999 | McCardel et al. |
| 5,980,734 A | 11/1999 | Itoh et al. |
| 5,980,757 A | 11/1999 | Brown et al. |
| 5,985,315 A | 11/1999 | Patat et al. |
| 5,997,544 A | 12/1999 | Nies et al. |
| 6,007,811 A | 12/1999 | Sawyer et al. |
| 6,010,627 A | 1/2000 | Hood, III |
| 6,011,490 A | 1/2000 | Tonnesen et al. |
| 6,020,196 A | 2/2000 | Hu et al. |
| 6,022,306 A | 2/2000 | Dumont et al. |
| 6,025,201 A | 2/2000 | Zelmanovic et al. |
| 6,027,655 A | 2/2000 | Holm |
| 6,049,026 A | 4/2000 | Muschler |
| 6,051,146 A | 4/2000 | Green et al. |
| 6,051,147 A | 4/2000 | Bischof |
| 6,053,856 A | 4/2000 | Hlavinka |
| 6,054,122 A | 4/2000 | MacPhee et al. |
| 6,063,297 A | 5/2000 | Antanavich et al. |
| 6,063,624 A | 5/2000 | Kandler et al. |
| 6,071,421 A | 6/2000 | Brown |
| 6,071,422 A | 6/2000 | Hlavinka et al. |
| 6,071,423 A | 6/2000 | Brown et al. |
| 6,090,793 A | 7/2000 | Zimmermann et al. |
| 6,096,309 A | 8/2000 | Prior et al. |
| 6,102,843 A | 8/2000 | Kelley et al. |
| 6,117,425 A | 9/2000 | MacPhee et al. |
| 6,123,655 A | 9/2000 | Fell et al. |
| 6,150,163 A | 11/2000 | McPherson et al. |
| 6,153,113 A | 11/2000 | Goodrich et al. |
| 6,183,737 B1 | 2/2001 | Zaleske et al. |
| 6,196,987 B1 | 3/2001 | Holmes et al. |
| 6,197,325 B1 | 3/2001 | MacPhee et al. |
| 6,200,287 B1 | 3/2001 | Keller et al. |
| 6,200,606 B1 | 3/2001 | Peterson et al. |
| 6,214,338 B1 | 4/2001 | Antanavich et al. |
| 6,221,315 B1 | 4/2001 | Giesler et al. |
| 6,245,900 B1 | 6/2001 | Yamasaki et al. |
| 6,264,890 B1 | 7/2001 | Boehringer et al. |
| 6,274,090 B1 | 8/2001 | Coelho et al. |
| 6,277,961 B1 | 8/2001 | Hock et al. |
| 6,280,400 B1 | 8/2001 | Niermann |
| 6,286,670 B1 | 9/2001 | Smith |
| 6,296,602 B1 | 10/2001 | Headley |
| 6,316,247 B1 | 11/2001 | Katz et al. |
| 6,322,785 B1 | 11/2001 | Landesberg et al. |
| 6,327,491 B1 | 12/2001 | Franklin et al. |
| 6,328,765 B1 | 12/2001 | Hardwick et al. |
| 6,334,842 B1 | 1/2002 | Hlavinka et al. |
| 6,342,157 B1 | 1/2002 | Hood, III |
| 6,351,659 B1 | 2/2002 | Vilsmeier |
| 6,355,239 B1 | 3/2002 | Bruder et al. |
| 6,368,298 B1 | 4/2002 | Beretta et al. |
| 6,368,498 B1 | 4/2002 | Guilmette |
| 6,398,972 B1 | 6/2002 | Blasetti et al. |
| 6,406,671 B1 | 6/2002 | DiCesare et al. |
| 6,409,528 B1 | 6/2002 | Bodnar |
| 6,410,344 B1 | 6/2002 | Chung |
| 6,417,004 B1 | 7/2002 | Brady et al. |
| 6,440,444 B2 | 8/2002 | Boyce et al. |
| 6,444,228 B1 | 9/2002 | Baugh et al. |
| 6,464,624 B2 | 10/2002 | Pages |
| 6,471,069 B2 | 10/2002 | Lin et al. |
| 6,472,162 B1 | 10/2002 | Coelho et al. |
| 6,487,992 B1 | 12/2002 | Hollis |
| 6,508,778 B1 | 1/2003 | Verkaart et al. |
| 6,516,953 B1 | 2/2003 | DiCesare et al. |
| 6,523,698 B1 | 2/2003 | Dennehey et al. |
| 6,544,162 B1 | 4/2003 | Van Wie et al. |
| 6,544,727 B1 | 4/2003 | Hei |
| 6,558,341 B1 | 5/2003 | Swisher |
| 6,563,953 B2 | 5/2003 | Lin et al. |
| 6,596,180 B2 | 7/2003 | Baugh et al. |
| 6,623,959 B2 | 9/2003 | Harris |
| 6,629,919 B2 | 10/2003 | Egozy et al. |
| 6,638,503 B2 | 10/2003 | Chitte et al. |
| 6,676,629 B2 | 1/2004 | Andrew et al. |
| 6,716,187 B1 | 4/2004 | Jorgensen et al. |
| 6,719,901 B2 | 4/2004 | Dolecek et al. |
| 6,733,471 B1 | 5/2004 | Ericson et al. |
| 6,758,978 B1 | 7/2004 | Bedell |
| 6,764,531 B2 | 7/2004 | Hogan |
| 6,777,231 B1 | 8/2004 | Katz et al. |
| 6,803,022 B2 | 10/2004 | DiCesare et al. |
| 6,811,777 B2 | 11/2004 | Mishra |
| 6,830,762 B2 | 12/2004 | Baugh et al. |
| 6,835,353 B2 | 12/2004 | Smith et al. |
| 6,835,377 B2 | 12/2004 | Goldberg et al. |
| RE38,730 E | 4/2005 | Wells et al. |
| 6,899,813 B2 | 5/2005 | Dolecek et al. |
| 6,905,612 B2 | 6/2005 | Dorian et al. |
| 6,911,202 B2 | 6/2005 | Amir et al. |
| RE38,757 E | 7/2005 | Wells et al. |
| 6,979,307 B2 | 12/2005 | Beretta et al. |
| 7,011,644 B1 | 3/2006 | Andrew et al. |
| 7,077,273 B2 | 7/2006 | Ellsworth et al. |
| 7,077,827 B2 | 7/2006 | Greenfield |
| 7,155,288 B2 | 12/2006 | Soykan et al. |
| 7,179,391 B2 | 2/2007 | Leach et al. |
| 7,195,606 B2 | 3/2007 | Ballin |
| 7,223,346 B2 | 5/2007 | Dorian et al. |
| 7,273,886 B2 | 9/2007 | Olivero et al. |
| 7,354,515 B2 | 4/2008 | Coull et al. |
| 7,374,678 B2 | 5/2008 | Leach et al. |
| 7,411,006 B2 | 8/2008 | Shanbrom |
| 7,470,371 B2 | 12/2008 | Dorian et al. |
| 7,531,355 B2 | 5/2009 | Rodriguez et al. |
| 7,553,413 B2 | 6/2009 | Dorian et al. |
| 7,694,828 B2 | 4/2010 | Swift et al. |
| 7,780,860 B2 | 8/2010 | Higgins et al. |
| 7,806,276 B2 | 10/2010 | Leach et al. |
| 7,832,566 B2 | 11/2010 | Leach et al. |
| 7,837,884 B2 | 11/2010 | Dorian et al. |
| 7,845,499 B2 | 12/2010 | Higgins et al. |
| 7,850,651 B2 | 12/2010 | Allee et al. |
| 7,901,584 B2 | 3/2011 | Dorian et al. |
| 7,914,689 B2 | 3/2011 | Higgins et al. |
| 7,954,646 B2 | 6/2011 | Leach et al. |
| 7,987,995 B2 | 8/2011 | Dorian et al. |
| 7,992,725 B2 | 8/2011 | Leach et al. |
| 8,048,321 B2 | 11/2011 | Leach et al. |
| 8,062,534 B2 | 11/2011 | Higgins et al. |
| 8,067,534 B2 | 11/2011 | Jagota et al. |
| 8,119,013 B2 | 2/2012 | Leach et al. |
| 8,163,184 B2 | 4/2012 | Leach et al. |
| 8,187,477 B2 | 5/2012 | Dorian et al. |
| 8,313,954 B2 | 11/2012 | Leach et al. |
| 8,328,024 B2 | 12/2012 | Leach et al. |
| 8,474,630 B2 | 7/2013 | Dorian et al. |

(56) References Cited

U.S. PATENT DOCUMENTS

| | | |
|---|---|---|
| 8,567,609 B2 | 10/2013 | Landrigan et al. |
| 8,596,470 B2 | 12/2013 | Leach et al. |
| 2001/0009757 A1 | 7/2001 | Bischof et al. |
| 2002/0032112 A1 | 3/2002 | Pages |
| 2002/0035820 A1 | 3/2002 | Farris |
| 2002/0076400 A1 | 6/2002 | Katz et al. |
| 2002/0082220 A1 | 6/2002 | Hoemann et al. |
| 2002/0090711 A1 | 7/2002 | Karlsson |
| 2002/0104808 A1 | 8/2002 | Blasetti et al. |
| 2002/0114775 A1 | 8/2002 | Pathak |
| 2002/0161449 A1 | 10/2002 | Muschler |
| 2002/0169408 A1 | 11/2002 | Beretta et al. |
| 2002/0172666 A1 | 11/2002 | Sacchi et al. |
| 2002/0182664 A1 | 12/2002 | Dolecek et al. |
| 2002/0192632 A1 | 12/2002 | Hei et al. |
| 2003/0033021 A1 | 2/2003 | Plouhar et al. |
| 2003/0033022 A1 | 2/2003 | Plouhar et al. |
| 2003/0050709 A1 | 3/2003 | Noth et al. |
| 2003/0050710 A1 | 3/2003 | Petersen et al. |
| 2003/0082152 A1 | 5/2003 | Hedrick et al. |
| 2003/0185803 A1 | 10/2003 | Kadiyala et al. |
| 2003/0191429 A1 | 10/2003 | Andrew et al. |
| 2003/0205538 A1 | 11/2003 | Dorian et al. |
| 2004/0005246 A1 | 1/2004 | Efthimiadis et al. |
| 2004/0013575 A1 | 1/2004 | Stevens et al. |
| 2004/0120942 A1 | 6/2004 | McGinnis et al. |
| 2004/0171146 A1 | 9/2004 | Katz et al. |
| 2004/0182395 A1 | 9/2004 | Brookman |
| 2004/0182788 A1 | 9/2004 | Dorian et al. |
| 2004/0182795 A1 | 9/2004 | Dorian et al. |
| 2004/0251217 A1 | 12/2004 | Leach et al. |
| 2005/0076396 A1 | 4/2005 | Katz et al. |
| 2005/0084961 A1 | 4/2005 | Hedrick et al. |
| 2005/0084962 A1 | 4/2005 | Simon |
| 2005/0109716 A1 | 5/2005 | Leach et al. |
| 2005/0130301 A1 | 6/2005 | McKay et al. |
| 2005/0145187 A1 | 7/2005 | Gray |
| 2005/0153441 A1 | 7/2005 | Hedrick et al. |
| 2005/0153442 A1 | 7/2005 | Katz et al. |
| 2005/0186120 A1 | 8/2005 | Dorian et al. |
| 2005/0196393 A1 | 9/2005 | Shanbrom |
| 2005/0196874 A1 | 9/2005 | Dorian et al. |
| 2005/0247715 A1 | 11/2005 | Ellsworth et al. |
| 2005/0260174 A1 | 11/2005 | Fraser et al. |
| 2005/0260175 A1 | 11/2005 | Hedrick et al. |
| 2005/0282275 A1 | 12/2005 | Katz et al. |
| 2006/0051865 A1 | 3/2006 | Higgins et al. |
| 2006/0057693 A1 | 3/2006 | Simon |
| 2006/0083720 A1 | 4/2006 | Fraser et al. |
| 2006/0140923 A1 | 6/2006 | Evangelista et al. |
| 2006/0151384 A1 | 7/2006 | Ellsworth et al. |
| 2006/0175242 A1 | 8/2006 | Dorian et al. |
| 2006/0175244 A1 | 8/2006 | Dorian et al. |
| 2006/0178610 A1 | 8/2006 | Nowakowski |
| 2006/0196885 A1 | 9/2006 | Leach et al. |
| 2006/0243676 A1 | 11/2006 | Swift et al. |
| 2006/0273049 A1 | 12/2006 | Leach et al. |
| 2006/0273050 A1 | 12/2006 | Higgins et al. |
| 2006/0278588 A1 | 12/2006 | Woodell-May |
| 2007/0034579 A1 | 2/2007 | Dorian et al. |
| 2007/0036768 A1 | 2/2007 | Fraser et al. |
| 2007/0075016 A1 | 4/2007 | Leach |
| 2007/0208321 A1 | 9/2007 | Leach et al. |
| 2008/0011684 A1 | 1/2008 | Dorian et al. |
| 2008/0164204 A1 | 7/2008 | Hatamian et al. |
| 2008/0173593 A1 | 7/2008 | Coull et al. |
| 2008/0193424 A1 | 8/2008 | McKale et al. |
| 2008/0210645 A1 | 9/2008 | Coull et al. |
| 2008/0217263 A1 | 9/2008 | Higgins et al. |
| 2008/0217264 A1 | 9/2008 | Leach et al. |
| 2008/0217265 A1 | 9/2008 | Leach et al. |
| 2008/0268064 A1 | 10/2008 | Woodell-May |
| 2008/0269762 A1 | 10/2008 | Simon et al. |
| 2008/0283474 A1 | 11/2008 | Leach et al. |
| 2008/0306431 A1 | 12/2008 | Yoo |
| 2008/0318317 A1 | 12/2008 | Roche et al. |
| 2009/0014391 A1 | 1/2009 | Leach et al. |
| 2009/0018313 A1 | 1/2009 | Shanbrom |
| 2009/0101599 A1 | 4/2009 | Dorian et al. |
| 2009/0192528 A1 | 7/2009 | Higgins et al. |
| 2009/0220482 A1 | 9/2009 | Higgins et al. |
| 2009/0221075 A1 | 9/2009 | Dorian et al. |
| 2009/0236297 A1 | 9/2009 | Dorian et al. |
| 2009/0250413 A1 | 10/2009 | Hoeppner |
| 2009/0253566 A1 | 10/2009 | Chavarria |
| 2009/0289014 A1 | 11/2009 | Hoeppner |
| 2010/0055087 A1 | 3/2010 | Higgins et al. |
| 2010/0140182 A1 | 6/2010 | Chapman et al. |
| 2010/0186676 A1 | 7/2010 | Van Der Berg |
| 2010/0206798 A1 | 8/2010 | Dorian et al. |
| 2010/0256595 A1 | 10/2010 | Leach et al. |
| 2010/0323870 A1 | 12/2010 | Leach et al. |
| 2010/0324450 A1 | 12/2010 | Leach et al. |
| 2011/0014705 A1 | 1/2011 | Leach et al. |
| 2011/0020196 A1 | 1/2011 | Grippi et al. |
| 2011/0021334 A1 | 1/2011 | Leach et al. |
| 2011/0036786 A1 | 2/2011 | Ellsworth |
| 2011/0056893 A1 | 3/2011 | Leach et al. |
| 2011/0065183 A1 | 3/2011 | Dorian et al. |
| 2011/0077596 A1 | 3/2011 | Higgins et al. |
| 2011/0168193 A1 | 7/2011 | Leach et al. |
| 2011/0192804 A1 | 8/2011 | Landrigan et al. |
| 2011/0251041 A1 | 10/2011 | Chavarria et al. |
| 2012/0015796 A1 | 1/2012 | Leach et al. |
| 2012/0145652 A1 | 6/2012 | Leach et al. |
| 2012/0228203 A1 | 9/2012 | Hecker et al. |
| 2013/0068676 A1 | 3/2013 | Leach et al. |
| 2013/0102452 A1 | 4/2013 | Leach et al. |
| 2013/0196425 A1 | 8/2013 | Dorian et al. |
| 2013/0294983 A1 | 11/2013 | Dorian et al. |
| 2014/0051061 A1 | 2/2014 | Landrigan et al. |
| 2014/0054246 A1 | 2/2014 | Landrigan et al. |
| 2014/0091048 A1 | 4/2014 | Leach et al. |
| 2014/0275497 A1 | 9/2014 | Leach et al. |
| 2014/0349388 A1 | 11/2014 | Dorian et al. |
| 2014/0356446 A1 | 12/2014 | Leach et al. |

FOREIGN PATENT DOCUMENTS

| | | |
|---|---|---|
| CA | 1321138 | 8/1993 |
| CA | 2182862 | 6/1996 |
| CA | 2448415 A1 | 12/2002 |
| CN | 1074709 | 7/1993 |
| CN | 1321103 A | 11/2001 |
| CN | 1322146 A | 11/2001 |
| CN | 103702729 A | 4/2014 |
| DE | 56103 | 10/1860 |
| DE | 1443359 | 11/1968 |
| DE | 4202667 | 5/1993 |
| EP | 090997 | 10/1983 |
| EP | 0102773 | 3/1984 |
| EP | 0109374 | 5/1984 |
| EP | 0142339 | 5/1985 |
| EP | 0244834 A2 | 11/1987 |
| EP | 0253198 | 1/1988 |
| EP | 0295771 | 12/1988 |
| EP | 0417818 | 3/1991 |
| EP | 534178 | 3/1993 |
| EP | 0534178 | 3/1993 |
| EP | 0592242 | 4/1994 |
| EP | 1005910 | 6/2000 |
| EP | 1006360 A2 | 6/2000 |
| EP | 1289618 | 3/2003 |
| EP | 1406492 B1 | 4/2004 |
| EP | 1427279 A1 | 6/2004 |
| EP | 1467746 A2 | 10/2004 |
| EP | 1509326 | 3/2005 |
| EP | 1670315 A2 | 6/2006 |
| EP | 1716901 | 11/2006 |
| GB | 854715 | 11/1960 |
| JP | 60-053845 | 3/1985 |
| JP | 60250014 A | 12/1985 |
| JP | 2036872 | 2/1990 |
| JP | 02071747 | 3/1990 |

(56) References Cited

FOREIGN PATENT DOCUMENTS

| | | |
|---|---|---|
| JP | 2000199760 A | 7/2000 |
| JP | 02129224 | 10/2000 |
| JP | 2004-305439 A | 11/2004 |
| JP | 2005013783 A | 1/2005 |
| JP | 200598704 | 4/2005 |
| JP | 2005524451 | 8/2005 |
| JP | 2006-305365 A | 11/2006 |
| JP | 2006527025 A | 11/2006 |
| JP | 2008104789 A | 5/2008 |
| WO | WO-8400905 | 3/1984 |
| WO | WO-8802259 | 4/1988 |
| WO | WO-9010031 | 9/1990 |
| WO | WO-9222312 | 12/1992 |
| WO | WO-9305067 | 3/1993 |
| WO | WO-9308904 | 5/1993 |
| WO | WO-9407548 | 4/1994 |
| WO | WO-9617871 | 6/1996 |
| WO | WO-9617871 A1 | 6/1996 |
| WO | WO-9848938 A1 | 11/1998 |
| WO | WO-0061256 | 10/2000 |
| WO | WO-0074713 A1 | 12/2000 |
| WO | WO-0103756 | 1/2001 |
| WO | WO-0183068 | 11/2001 |
| WO | WO-0238610 A1 | 5/2002 |
| WO | WO-02060925 A1 | 8/2002 |
| WO | WO-02098566 A2 | 12/2002 |
| WO | WO-03015800 | 2/2003 |
| WO | WO-03024215 A1 | 3/2003 |
| WO | WO-03053362 A2 | 7/2003 |
| WO | WO-03088905 | 10/2003 |
| WO | WO-03092894 | 11/2003 |
| WO | WO-03099412 A1 | 12/2003 |
| WO | WO-2004009207 | 1/2004 |
| WO | WO-2004104553 | 12/2004 |
| WO | WO-2005034843 A2 | 4/2005 |
| WO | WO-2006041406 A1 | 4/2006 |
| WO | WO-2007127834 A2 | 11/2007 |
| WO | WO-2007142908 A1 | 12/2007 |
| WO | WO-2008127639 A1 | 10/2008 |
| WO | WO-2009021257 A1 | 2/2009 |
| WO | WO-2009111338 A1 | 9/2009 |
| WO | WO-2011008836 A1 | 1/2011 |

OTHER PUBLICATIONS

"Caps for Corning® and Costar® Plastic Labware," Technical Bulletin. (Dec. 2008) Corning, Incorporated.
"Cell Isolation Techniques, Methods and Materials, Working with Enzymes," (2004) (9 pages) Worthington Biochemical Corp.
"Cell Isolation Theory, Tissue Types," (2004) (5 pages) Worthington Biochemical Corp.
"Centrifuge Tubes" CORNING Costar brochure. 1996/1997 Catalog pp. 76-77.
"Clotalyst® Autologous Clotting Factor" brochure. (Aug. 15, 2008) Biomet Biologics.
"Clotalyst® Autologous Clotting Factor. Would you like to have an autologous thrombin for rapid clotting and haemostasis?" Brochure. Biomet Biologics (Aug. 15, 2008).
"Corning® 15 and 50 mL Centrifuge Tubes," Life Sciences. (Jun. 2005) Corning Incorporated.
"Cytori Celution Cell Concentrate Device," Exhibit 14, 510(k) Summary, FDA approval K060482 (Sep. 28, 2006).
"Frequently Asked Questions, 1. Kits, 2. Enzymes," (2003) 3 pages Worthington Biochemical Corp.
"Letter CryoSeal FS System. Vaccines, Blood & Biologics," letter. (Jul. 26, 2007) FDA U.S. Food and Drug Administation. http://www.fda.gov/BiologicsBloodVaccines/BloodBloodProducts/ApprovedProducts/Premarket ApprovalsPMAs/ucm091631.htm (Web accessed Aug. 12, 2011).
"MarrowStim™ Concentration Kit Peripheral Arterial Disease (PAD) Study" brochure. Web. Jul. 2, 2009 http://www.biomet.com/patients/clinical_recruitment_padstudy.cfm.
"MarrowStim™ Concentration System," brochure. Biomet Biologics Jun. 15, 2008.
"Plasmax® Plasma Concentration System" brochure. (Jun. 15, 2008) Biomet® Biologics.
"Prosys PRP Kit," brochure Tozai Holdings, Inc. http://tozaiholdings.en.ec21.com/Prosys_PRP_Kit--5467051_5467061.html Printed from Web Aug. 24, 2011.
"Prosys PRP Kit," Tozai Holdings, Inc. EC21 Global B2B Marketplace http://www.ec21.com/product-details/Prosys-PRP-Kit--5467061.html Printed from Web Jul. 18, 2011.
"ThermoGenesis Corp. to Supply Autologous Thrombin Kits to Biomet, Inc.," PR Newslink: http://tinyurl.com/4h3up. (Apr. 5, 2005) http://www.noblood.org/press-releases/2128-thermogenesis-corp-supply-autologous-thrombin-kits-biomet-inc [web accessed Sep. 27, 2011].
"Trypsinizing cells." Bart's Cookbook, Web. Apr. 14, 2010. http://pingu.salk.edu/~sefton/Hyper_protocols/trypsin.html.
Anesthesiology, vol. 81, No. 4, pp. 1074-1077, Oct. 1994, Hiromasa Mitsuhata, M.D., et al., "An Anaphylactic Reaction to Topical Fibrin Glue".
Ann Thorac Surg, vol. 53, pp. 530-531, 1992, Mehmet C. Oz, M.D., et al., "Autologous Fibrin Glue From Intraoperatively Collected Platelet-Rich Plasma".
Ann Thorac Surg, vol. 56, pp. 387-389, 1993, Robert L. Quigley, M.D., et al., "Intraoperative Procurement of Autologous Fibrin Glue".
Badivas, et al., "Treatment of Chronic Wounds With Bone Marrow-Derived Cells," (Reprinted) Arch Dermatol. 139:510-516 (Apr. 2003).
Bang, N.U., et al., "Plasma Protein Requirements for Human Platelet Aggregation" Ann. N.Y. Acad Sci, 201:280-299 (1972).
Berguer, R., R. L. Staerkel, E. E. Moore, F. A. Moore, W. B. Galloway, and M. B. Mockus. "Warning: fatal reaction to the use of fibrin glue in deep hepatic wounds. Case reports." *J Trauma* 31:3 (1991): 408-11.
Berruyer, M., J. Amiral, P. Ffrench, J. Belleville, O. Bastien, J. Clerc, A. Kassir, S. Estanove, and M. Dechavanne. "Immunization by bovine thrombin used with fibrin glue during cardiovascular operations. Development of thrombin and factor V inhibitors," *J Thorac Cardiovasc Surg* 105: 5 (1993): 892-7.
BioCUE™ Platelet Concentration System, Jun. 2010. (2 pages).
Biopolymers, vol. 27, pp. 763-774, 1988, Gerald Marx, "Mechanism of Fibrin Coagulation Based on Selective, Cation-Driven, Protofibral Association".
Boomgaard, et al., "Pooled Platelet Concentrates Prepared by the Platelet-Rich-Plasma Method and Filtered with Three Different Filters and Stored for 8 Days." Vox Sanq, vol. 68: 82-89, Feb. 1995.
Brodke, et al., "Bone Grafts Prepared with Selective Cell Retention Technology Heal Canine Segmental Defects as Effectively as Autograft", SCR-Enriched Bone Grafts Heal Canine Segmental Defects, Journal of Orthopaedic Research (May 2006) pp. 857-866.
Casali, B., F. Rodeghiero, A. Tosetto, B. Palmieri, R. Immovilli, C. Ghedini, and P. Rivasi. "Fibrin glue from single-donation autologous plasmapheresis." Transfusion 32:7 (1992): 641-3.
Clotalyst™ Automatic Clotting Factor, Would you like to have an autologous thrombin for rapid clotting and haemostasis?, brochure, Biomet Biologics, Inc., Feb. 2007 (12 pages).
Connolly, "Injectable Bone Marrow Preparations to Stimulate Osteogenic Repair," Clinical Orthopaedics and Related Research 313:8-18 (Apr. 1995).
Connolly, John, M.D., et al. "Development of an Osteogenic Bone-Marrow Preparation." The Journal of Bone and Joint Surgery, Incorporated. vol. 71-A, No. 5 (Jun. 1989) pp. 684-691.
Dallari, et al., "In Vivo Study on the Healing of Bone Defects Treated with Bone Marrow Stromal Cells, Platelet-Rich Plasma, and Freeze-Dried Bone Allografts, Alone and in Combination," Healing of Bone Defects, Journal of Orthopaedic Research (May 2006) pp. 877-888.
De Ugarte, et al., "Comparison of Multi-Lineage Cells from Human Adipose Tissue and Bone Marrow," Cells Tissues Organs 174:101-109 (2003).
De Wit, et al. "Experiments on the Preparation of Blood Components with the IBM 2991 Blood Cell Processor" Vox Sang. 29: 352-362 (Feb. 10, 1975).

(56) References Cited

OTHER PUBLICATIONS

DelRossi, A. J., A. C. Cernaianu, R. A.Vertrees, C. J. Wacker, S. J. Fuller, J. Cilley Jr., and W. A. Baldino. "Platelet-rich plasma reduces postoperative blood loss after cardiopulmonary bypass." *J Thorac Cardiovasc Surg* 100:2 (Aug. 1990): 281-6.
DePalma, L., et al., "The preparation of fibrinogen concentrate for use as fibrin glue by four different methods." Transfusion (1993) vol. 33, No. 9; pp. 717-720.
DeUgarte, M.D., Daniel A., et al., "Future of Fat as Raw Material for Tissue Regeneration," (Feb. 2003) pp. 215-219, Lippincott Williams & Wilkins, Inc.
DiMuzio, Paul et al., "Development of a Tissue-Engineered Bypass Graft Seeded with Stem Cells," Vasucular, vol. 14, No. 6, (2006) pp. 338-342, BC Decker, Inc.
Drug Intelligence and Clinical Pharmacy, vol. 22, pp. 946-952, Dec. 1988, Dennis F. Thompson, et al., "Fibrin Glue: A Review of Its Preparation, Efficacy, and Adverse Effects as a Topical Hemostat".
Edlich, Richard F., George T. Rodeheaver, and John G. Thacker. "Surgical Devices in Wound Healing Management." In *Wound Healing: Biochemical & Clinical Aspects*,ed. I. Kelman Cohen, Robert F. Diegelmann, and William J. Lindblad. 581-600. 1st ed., vol. Philadelphia: W.B. Saunders Company, 1992.
Eppley, et al., "Platelet Quantification and Growth Factor Analysis from Platelet-Rich Plasma: Implications for Wound Healing," Plastic and Reconstructive Surgery, 114(6):1502-1508 (Nov. 2004).
Epstein, G. H., R. A. Weisman, S. Zwillenberg, and A. D. Schreiber. "A new autologous fibrinogen-based adhesive for otologic surgery." *Ann Otol Rhinol Laryngol* 95 (May 25-26, 1985) 40-5.
Fibrostik™ Plasma Concentrator, Attention Operating Surgeon, Cell Factor Technologies, Inc., Jul. 2003.
First clinical results: Kuderma, H. and Helene Matras. "Die klinische Anwendung der Klebung van Nervenanastomosen mit Gerinnungssubstanzen bei der Rekonstruction verletzter peripherer Nerven." Wein Klin Wochenschr 87 (Aug. 15, 1975): 495-501.
Floryan, K. et al. "Home Study Program: Intraoperative Use of Autologous Platelet-Rich and Platelet-Poor Plasma for Orthopedic Surgery Patients" vol. 80, No. 4 (Oct. 2004) p. 667-674.
Frasier, John K., et al., "Plasticity of human adipose stem cells toward endothelial cells and cardiomyocytes," Nature Clinical Practice Cardiovascular Medicine, vol. 3, Supplement 1 (Mar. 2006) pp. S33-S37.
Friesen, M.D., Robert, et al. "Blood Conservation During Pediatric Cardiac Surgery: Ultrafiltration of the Extracorporeal Circuit Volume After Cardiopulmonary Bypass." Anesth. Analg 1993: 77-702-7.
Galois, et al., "Cartilage Tissue Engineering: State-of-the-Art and Future Approaches," Pathol Biol (Paris), 53(10), Dec. 2005.
Gibble, J. W. and P. M. Ness. "Fibrin glue: the perfect operative sealant?" *Transfusion* 30 (1990): 741-7.
Gimble, Jeffrey M., "Adipose-Derived Stem Cells for Regenerative Medicine," Circulation Research (May 11, 2007) pp. 1249-1260, American Heart Association, Inc.
Gomillion, Cheryl T., et al., "Stem cells and adipose tissue engineering," Biomaterials 27, Science Direct (2006) pp. 6052-6063, Elsevier.
Gps® III System, GPS® III Platelet Separation System, Leadership through Technology, brochure, Jul. 2007 (8 sheets).
GPS® System, "GPS® Platelet Concentrate System," Cell Factor Technologies, Inc., Biomet Orthopaedics, Inc., (Feb. 29, 2004) (9 pages).
GPS® System, "Shoulder Recovery with the GPS® Platelet Concentrate System, Rotator Cuff Surgical Techniques," brochure, Cell Factor Technologies, Inc., Biomet Orthopaedics, Inc., (2004) 6 pages.
GPS® System, "Shoulder Recovery with the GPS® Platelet Concentrate System, Rotator Cuff Surgical Techniques," Cell Factor Technologies, Inc., Biomet Orthopaedics, Inc., (2004) 3 pages, http://www.cellfactortech.com/global_products.cfm, printed Sep. 16, 2005.
Gps® II System, Gravitational Platelet Separation System, "Accelerating the Body's Natural Healing Process," Biomet Biologics (Jul. 15, 2006) 16 pages.
GPS® II System, Gravitational Platelet Separation System, "Accelerating the Body's Natural Healing Process," Cell Factor Technologies, Inc., Biomet Europe (2005) 16 pages, http://www.cellfactortech.com/global_products.cfm, printed Sep. 16, 2005.
GPS® II System, Gravitational Platelet Separation System, "User Manual," Cell Factor Technologies, Inc., Biomet Europe [date unknown] 13 pages, http://www.cellfactortech.com/global_products.cfm, printed Sep. 16, 2005.
Grove, et al., "Plasticity of Bone Marrow-Derived Stem Cells," Stem Cells: Concise Review, 22, Jan. 2004.
Guilak, Frank, et al., "Adipose-derived adult stem cells for cartilage tissue engineering," Biorheology 41 (2004) pp. 389-399, IOS Press.
Harris, E.L.V. Concentration of the Extract. In. Protein Purification Methods: A Practical Approach Harris, E.L.V.; Angal, S.; Editors. (1989) Publisher: (IRL Press, Oxford, UK), pp. 67-69.
Hartman, A. R., D. K. Galanakis, M. P. Honig, F. C. Seifert, and C. E. Anagnostopoulos. "Autologous whole plasma fibrin gel. Intraoperative procurement." *Arch Surg* 127 (Mar. 1992): 357-9.
Harvest Technologies brochure, SmartPrep2 (2002).
Hattori, et al., "Osteogenic Potential of Human Adipose Tissue-Derived Stromal Cells as an Alternative Stem Cell Source," Cells Tissues Organs (2004) 178:2-12 Karger.
Haynesworth, S.E. et al. "Mitogenic Stimulation of Human Mesenchymal Stem Cells by Platelet Releasate Suggests a Mechanism for Enhancement of Bone Repair by Platelet Concentrate" 48th Annual Meeting of the Orthopaedic Research Society Poster No. 0462 (2002).
Hennis, H. L., W. C. Stewart, and E. K. Jeter. "Infectious disease risks of fibrin glue [letter]." *Ophthalmic Surg* 23 (Sep. 1992): 640.
Hernigou, et al., "Percutaneous Autologous Bone-Marrow Grafting for Nonunions. Influence of the Number and Concentration of Progenitor Cells," Journal of Bone & Joint Surgery, 87-A(7):1430-1437 (Jul. 2005).
Hom, D., et al. "Promoting Healing with Recombinant Human Platelet-Derived Growth Factor-BB in a Previously Irradiated Problem Wound." The Laryngoscope, vol. 113 (pp. 1566-1671) Sep. 2003.
Hood, Andrew G., et al., "Perioperative Autologous Sequestration III: A New Physiologic Glue with Wound Healing Properties," (Jan. 1993) vol. 14 pp. 126-129.
International Preliminary Examination Report and Written Opinion issued Aug. 31, 2010 for PCT/US2009/035564 claiming benefit of U.S. Appl. No. 61/078,178, filed Jul. 3, 2008, which priority is also claimed of said provisional case by U.S. Appl. No. 12/395,085, filed Feb. 27, 2009.
International Preliminary Report on Patentability and Written Opinion mailed Oct. 13, 2011 for PCT/US2010/029957 which claims benefit of U.S. Appl. No. 12/417,789, filed Apr. 3, 2009.
International Preliminary Report on Patentability completed Aug. 13, 2009 for PCT/US2008/004687 claiming benefit of U.S. Appl. No. 60/911,407, filed Apr. 12, 2007.
International Preliminary Report on Patentability mailed Jan. 26, 2012 for PCT/US2010/041942 claiming benefit of U.S. Appl. No. 12/504,413, filed Jul. 16, 2009.
International Search Report and Written Opinion mailed Aug. 9, 2011 for PCT/US2011/031954 claiming benefit of U.S. Appl. No. 12/758,127, filed Apr. 12, 2010.
International Search Report and Written Opinion mailed Jul. 2, 2008 for International Application No. PCT/US2008/004687 which claims priority to U.S. Appl. No. 60/911,407, filed Apr. 12, 2007.
International Search Report and Written Opinion mailed Jul. 3, 2009 for PCT/US2009/035564 claiming benefit of U.S. Appl. No. 61/078,178, filed Jul. 3, 2008.
International Search Report and Written Opinion mailed Jul. 30, 2010 for PCT/US2010/029957 which claims benefit of U.S. Appl. No. 12/417,789, filed Apr. 3, 2009.
International Search Report and Written Opinion mailed Nov. 7, 2011 for PCT/US2011/045290 claiming benefit of U.S. Appl. No. 12/846,944, filed Jul. 30, 2010.
International Search Report and Written Opinion mailed Oct. 8, 2010 for PCT/US2010/041942 claiming benefit of U.S. Appl. No. 12/504,413, filed Jul. 16, 2009.

(56) References Cited

OTHER PUBLICATIONS

International Search Report for International Application No. PCT/US/0316506 mailed Oct. 13, 2003 which claims benefit of U.S. Appl. No. 60/383,013, filed May 24, 2002.
International Search Report for International Application No. PCT/US2007/012587 mailed Nov. 6, 2007 which claims benefit of U.S. Appl. No. 11/441,276, filed May 25, 2006.
Invitation to Pay Additional Fees and, Where Applicable, Protest Fee mailed Aug. 6, 2012 for PCT/US2012/034104 claiming benefit of U.S. Appl. No. 13/089,591, filed Apr. 19, 2011.
Ishida, et al., "Platelet-Rich Plasma With Biodegradable Gelatin Hydrogel Promotes Rabbit Meniscal Tissue Regeneration," 52nd Annual Meeting of the Orthopaedic Research Society Paper No. 1035, 1 page (2006).
Jackson, C. M. and Y. Nemerson. "Blood coagulation." *Annu Rev Biochem* 49 (1980): 765-811).
Japan Office Action mailed Jan. 22, 2013 for Japan Application No. 2010-503066.
Jayadev, Suprya. "Trypsinization of Adherent Cells." Aug. 8, 1991. Web. Apr. 14, 2010 http://www.duke.edu/web/ceramide/protocols/0005.html.
Johnstone, et al., "Autologous Mesenchymal Progenitor Cells in Articular Cartilage Repair", Clinical Orthopaedics and Related Research 367S:S156-S162 (Oct. 1999).
Jorgensen, et al., "Stem Cells for Repair of Cartilage and Bone: The Next Challenge in Osteoarthritis and Rheumatoid Arthritis," Annals of Rheumatic Diseases, Aug. 2000.
Journal of Oral Maxillofacial Surgery, vol. 43, pp. 605-611, Helene Matras, M.D., "Fibrin Seal: The State of the Art" (1985).
Karpatkin, S., "Heterogeneity of Human Platelets. VI., Correlation of Platelet Function with Platelet Volume", Blood, vol. 51, No. 2 (Feb. 1978).
Kjaergard, H. K., U. S. Weis-Fogh, H. Sorensen, J. Thiis, and I. Rygg. "A simple method of preparation of autologous fibrin glue by means of ethanol." *Surg Gynecol Obstet* 175 (1992): 72-3.
Kjaergard, H. K., Fogh Us Weis, and J. J. Thiis. "Preparation of autologous fibrin glue from pericardial blood." *Ann Thorac Sur* 55 (1993): 543-4.
Kumar, Vijay et al. "Stability of Human Thrombin Produced From 11 ml of Plasma Using the Thrombin Processing Device," Journal of American Society of Extra-Corporeal Technology. JECT: Mar. 2005:37; 390-395.
Kumar, Vijay et al. "Whole Blood Thrombin: Development of a Process for Intra-Operative Production of Human Thrombin." Journal of American Society of Extra-Corporeal Technology. JECT: Apr. 2007; 39:18-23.
Kumar, Vijay et al., "Autologous Thrombin: Intraoperative Production From Whole Blood." Journal of American Society of Extra-Corporeal Technology. JECT: Apr. 2008; 40:94-98.
Laryngoscope vol. 99, pp. 974-976, Sep. 1989, Kyosti Laitakari, M.D., et al., "Autologous and Homologous Fibrinogen Sealants: Adhesive Strength".
Laryngoscope, vol. 95, pp. 1074-1076, Sep. 1985, Karl H. Siedentop, M.D., et al., "Autologous Fibrin Tissue Adhesive".
Laryngoscope, vol. 96, pp. 1062-1064, Oct. 1986, Karl H. Siedentop, M.D., et al., "Extended Experimental and Preliminary Surgical Findings with Autologous Fibrin Tissue Adhesive Made from Patient's Own Blood".
Lasher, Lisa, M.D., "My Experience with PRP," PowerPoint presentation, http://www.cellfactortech.com/global_products.cfm, printed Sep. 16, 2005.
Lendeckel, Stefan, et al., "Autologous stem cells (adipose) and fibrin glue used to treat widespread traumatic calvarial defects: case report," Journal of Cranio-Maxillofacial Surgery (2004) European Association for Cranio-Maxillofacial Surgery.
Lerner, R. and N. S. Binur. "Current status of surgical adhesives." *J Surg Res* 48 (Feb. 1990): 165-81.
Longas, Maria O., "An Improved Method for the Purification of Human Fibrinogen." J. Biochem (1980) vol. 11, pp. 559-564.
Lu, et al., "Bone Marrow Mesenchymal Stem Cells: Progress in Bone/Cartilage Defect Repair," 19(1), Jan. 2002.
Marrowstim Concentration System, Biomet Biologics, Inc., 20 pages (REV Feb. 15, 2008).
Marx, Gerard, et al., "Heat Denaturation of Fibrinogen to Develop a Biomedical Matrix." Journal of Biomedical Materials Research Part B: Applied Biomaterials (Apr. 2007) pp. 49-57.
Masri, Marwan A., et al. "Isolation of Human Fibrinogen of High Purity and in High Yield Using Polyethylene Glycol 1000." Thromb Haemostas (Struttgart) (1983) vol. 49 (2); pp. 116-119.
Matras, Helene, H. P. Dinges, H. Lassmann, and B. Mamoli. "Zur nahtlosen interfaszikularen Nerventransplantation im Tierexperiment." Wein Med Woschtr 122:37 (1972): 517-523.
Minntech® Filtration Technologies Group, "Hemocor HPH® Hemoconcentrator," Minntech Corporation (2004); http://www.minntech.com/ftg/products/hph/index.html, printed Jul. 15, 2004 (2 pages).
Minntech® Filtration Technologies Group, "Medical Applications: Blood Filtration" Minntech Corporation (2004); http://www.minntech.com/ftg/industries/medical/blood_filter.html, printed Jul. 15, 2004 (1 page).
Minntech® Filtration Technologies Group, "Renaflo® II Hemofilter," Minntech Corporation (2004); http://www.minntech.com/ftg/products/renaflo/index.html, printed Jul. 15, 2004 (2 pages).
Molnar, Amy, "Stem Cells from Muscles Can Repair Cartilage, Study Finds Genetically Engineered Muscle-Derived Stem Cells Improved Cartilage Repair in Rats", American College of Rheumatology, (2005).
Moretz, W., Jr., J Shea Jr., J. R. Emmett, and J Shea. "A simple autologous fibrinogen glue for otologic surgery." *Otolaryngol Head Neck Surg* 95 (Jul. 1986): 122-4.
Nakagami, Hironori, et al., "Novel Autologous Cell Therapy in Ischemic Limb Disease Through Growth Factor Secretion by Cultured Adipose Tissue-Derived Stromal Cells," Angiogenesis by Adipose Tissue-Derived Cells, (Dec. 2005) pp. 2542-2547, American Heart Association, Inc.
Nathan, Suresh et al., "Cell-Based Therapy in the Repair of Osteochondral Defects: A Novel Use for Adipose Tissue," Tissue Engineering, vol. 9, No. 4 (2003) pp. 733-744 Mary Ann Liebert, Inc.
Nilsson, et al., "Bone Repair Induced by Bone Morphogenetic Protein in Ulnar Defects in Dogs," The Journal of Bone and Joint Surgery, vol. 68 B., No. 4, Aug. 1986.
Notice of Allowance mailed Mar. 24, 2011 for U.S. Appl. No. 12/101,586.
Notice of Allowance mailed May 27, 2010 for U.S. Appl. No. 12/101,594, filed Apr. 11, 2008.
Notice of Allowance mailed Oct. 18, 2011 for U.S. Appl. No. 12/897,401.
Office Action (Final) mailed Mar. 18, 2010 for U.S. Appl. No. 12/101,594 filed Apr. 11, 2008.
Office Action mailed Feb. 3, 2011 for U.S. Appl. No. 12/101,586, filed Apr. 14, 2008.
Office Action mailed Nov. 16, 2010 for U.S. Appl. No. 12/897,401 claiming benefit of U.S. Appl. No. 12/101,594, filed Apr. 11, 2008.
Office Action mailed Oct. 16, 2009 for U.S. Appl. No. 12/101,594, filed Apr. 11, 2008.
Office Action mailed Sep. 20, 2010 for U.S. Appl. No. 12/101,586, filed Apr. 14, 2008.
Orphardt, Charles E., "Denaturation of Proteins," Virtual Chembook, Elmhurst College (2003) 3 pages. http://www.elmhurst.edu/~chm/vchembook/568denaturation.html (web accessed Mar. 9, 2011).
Otolaryngologic Clinics of North America, vol. 27, No. 1, pp. 203-209, Feb. 1994, Dean M. Toriumi, M.D., et al., "Surgical Tissue Adhesives in Otolaryngology-Head and Neck Surgery".
Parker, Anna M., et al., Adipose-derived stem cells for the regeneration of damaged tissues, Expert Opinion, Cell- & Tissue-based Therapy, Expert Opin. Biol. Ther. (2006) pp. 567-578 Informa UK Ltd.
Planat-Bénard, V., et al., "Spontaneous Cardiomyocyte Differentiation From Adipose Tissue Stroma Cells," Adipose-Derived Cell Cardiomyocyte (Feb. 6, 2004) pp. 223-229 American Heart Association, Inc.

(56) References Cited

OTHER PUBLICATIONS

Ponticiello, Michael S., "A Rapid Technique for the Isolation and Concentration of Stem Cells from Human Bone Marrow", Cell Factor Technologies, Inc. (2006) 2 pages.
Rangappa, Sunil, M.D., "Transformation of Adult Mesenchymal Stem Cells Isolated From the Fatty Tissue Into Cardiomyocytes," Adult Stem Cells Transformed into Cardiomyoctyes, (2003) pp. 775-779 Ann Thorac Surg.
Rigotti, M.D., et al, "Clinical Treatment of Radiotherapy Tissue Damage by Lipoaspirate Transplant: A Healing Process Mediated by Adipose-Derived Adult Stem Cells," Plastic and Reconstructive Surgery, Breast, PRS Journal vol. 119, No. 5, Stem Cell Therapy for Angiogenesis, (Apr. 15, 2007) pp. 1409-1422.
Rubin, M.D., et al, "Clinical Treatment of Radiotherapy Tissue Damage by Lipoaspirate Transplant: A Healing Process Mediated by Adipose-Derived Adult Stem Cells," Plastic and Reconstructive Surgery, Discussion vol. 119, No. 5, Stem Cell Therapy for Angiogenesis, (Apr. 15, 2007) pp. 1423-1424.
Sanal, M. "Does fibrin glue cause foreign body reactions? [letter]." *Eur J Pediatr Surg* 3 (1992):190 (1 page).
Sanal, M., H. Dogruyol, A. Gurpinar, and O. Yerci. "Does fibrin glue cause foreign body reactions?" *Eu r J Pediatr Surg* 2 (1992): 285-6.
Schmidt, K.G., et al., "Labelling of Human and Rabbit Platelets with Indium-Oxine Complex", 23:97-106 (1979).
Schmidt, K.G., et al., "Preparation of Platelet Suspensions from Whole Blood in Buffer", Scand. J. Hoemato, 23:88-96 (1979).
Schäffler, Andreas, et al., "Concise Review: Adipose Tissue-Derived Stromal Cells—Basic and Clinical Implications for Novel Cell-Based Therapies," Tissue-Specific Stem Cells, Stem Cells® (Apr. 10, 2007) pp. 818-827 AlphaMed Press.
Semple, Elizabeth, PhD, et al. "Quality of Thrombin Produced From the Patient's Own Plasma Using the TPD™, a New Thrombin-Processing Device." Journal of American Society of Extra-Corporeal Technology. JECT: 2005; 37:196-200.
Sierra, D. H. "Fibrin sealant adhesive systems: a review of their chemistry, material properties and clinical applications." *J Biomater Appl* 7 (Apr. 1993): 309-52.
Sigma-Aldrich® Alkaline Phosphatase (Procedure No. 85), drug fact sheet, (2003) pp. 1-2, Sigma-Aldrich, Inc.
Silver, Frederick H., et al., "Review Preparation and use of fibrin glue in surgery." Biomaterials 16 (1995) pp. 891-903.
Solem, Jan Otto, et al., "Hemoconcentration by Ultrafiltration During Open-Heart Surgery," Scand J Thor Cardiovasc Surg 22:271-274, 1988.
Sutton, Robin G., et al. "Comparison of Three Blood-Processing Techniques During and After Cardiopulmonary Bypass." Ann Thorac Surg (1993) vol. 56; pp. 941-943.
Swift, Mathew J., et al., "Characterization of Growth Factors in Platelet Rich Plasma," 1-Cell Factor Technologies, http://www.cellfactortech.com/global_products.cfm, printed Sep. 16, 2005.
Symphony II Platelet Concentrate System/PCS brochure; "Increasing bone graft bioactivity through reproducible concentrations of natural growth factors," DePuy (Jan. 2003).
Takahashi, Kazutoshi et al., "Induction of Pluripotent Stem Cells from Adult Human Fibroblasts by Defined Factors," Cell, (Nov. 30, 2007) pp. 1-12, Elsevier Inc.
The American Journal of Surgery, vol. 168, pp. 120-122, Aug. 1994, Roy L. Tawes, Jr., M.D., et al., "Autologous Fibrin Glue: The Last Step in Operative Hemostatis".

The American Surgeon, vol. 55, pp. 166-168, Mar. 1989, William D. Spotnitz, M.D., et al., "Successful Use of Fibrin Glue During 2 Years of Surgery at a University Medical Center".
The Sports Medicine Center, "Knee Cartilage Implantation", Carticel™, "Autologous Cultured Chondrocyte Implantation", http://www.orthoassociates.com/carticel.htm (printed Apr. 6, 2006).
The Stone Clinic, "Platelet Rich Plasma (PRP)", web site printed May 2006.
Weis-Fogh, U. S. "Fibrinogen prepared from small blood samples for autologous use in a tissue adhesive system." *Eur Surg* Res 20 (1988): 381-9.
Weisman, MD., Robert A., "Biochemical Characterization of Autologous Fibrinogen Adhesive," Laryngoscope 97: Oct. 1987; pp. 1186-1190.
Wiseman, David M., David T. Rovee, and Oscar M. Alverez. "Wound Dressings: Design and Use." In *Wound Healing: Biochemical & Clinical Aspects*, ed. I. Kelman Cohen, Robert F. Diegelmann, and William J. Lindblad. 562-580. 1st ed., vol. Philadelphia: W. B. Saunders Company, 1992.
Woodell-May, et al., "Producing Accurate Platelet Counts for Platelet Rich Plasma: Validation of a Hematology Analyzer and Preparation Techniques for Counting," Scientific Foundation, Journal of Carniofacial Surgery 16(5):749-756 (Sep. 2005).
Written Opinion of the International Preliminary Examining Authority mailed Mar. 17, 2009 for International Application No. PCT/US2008/004687 which claims priority to U.S. Appl. No. 60/911,407, filed Apr. 12, 2007.
Yoon, Eulsik, M.D., Ph.D., et al., "In Vivo Osteogenic Potential of Human Adipose-Derived Stem Cells/Poly Lactide-Co-Glycolic Acid Constructs for Bone Regneration in a Rat Critical-Sized Calvarial Defect Model," Tissue Engineering, vol. 13, No. 3 (2007) pp. 619-627 Mary Ann Liebert, Inc.
Zhang, Duan-zhen, et al., "Transplantation of autologous adipose-derived stem cells ameliorates cardiac function in rabbits with myocardial infarction," Chinese Medical Journal, vol. 120, No. 4 (2007) pp. 300-307 General Hospital of Shenyang Military Region, Shenyang, China.
Zuk, Patricia A., Ph.D., "Multilineage Cells from Human Adipose Tissue: Implications for Cell-Based Therapies," Tissue Engineering, vol. 7, No. 2, (2001) pp. 211-228 Mary Ann Liebert, Inc.
International Search Report and Written Opinion mailed Dec. 5, 2013 for PCT/US2013/056793 claiming benefit of U.S. Appl. No. 13/595,461, filed Aug. 27, 2012.
Japanese Office Action mailed May 20, 2014 for Japanese Application No. JP2012-503768.
Chinese Office Action mailed Jun. 30, 2014 for Chinese Patent Application No. 201080019707.7, which claims benefit of PCT/US2010/029957 filed Apr. 5, 2010, which claims benefit of U.S. Appl. No. 12/417,789, filed Apr. 3, 2009.
Minivalve international: duckbill valves—du 054.001 sd, <http://www.minivalve.com/htm/DV054.htm>, Accessed Jun. 30, 2014, 1 page.
Momentive Silopren*LSR 2050, Jun. 30, 2014, 3 pages.
Vernay Product Information Sheet, Umbrella Check Valve, Part No. V251010200, Jul. 2013, 2 pages.
Chinese Office Action mailed Nov. 21, 2014 for Chinese Patent Application No. 201280030026.X.
Japanese Office Action mailed Sep. 9, 2014 for Japan Patent Application No. 2012-520742,which claims benefit of PCT/US2010/041942 filed Jul. 14, 2010, which claims benefit of U.S. Appl. No. 12/504,413, filed Jul. 16, 2009.

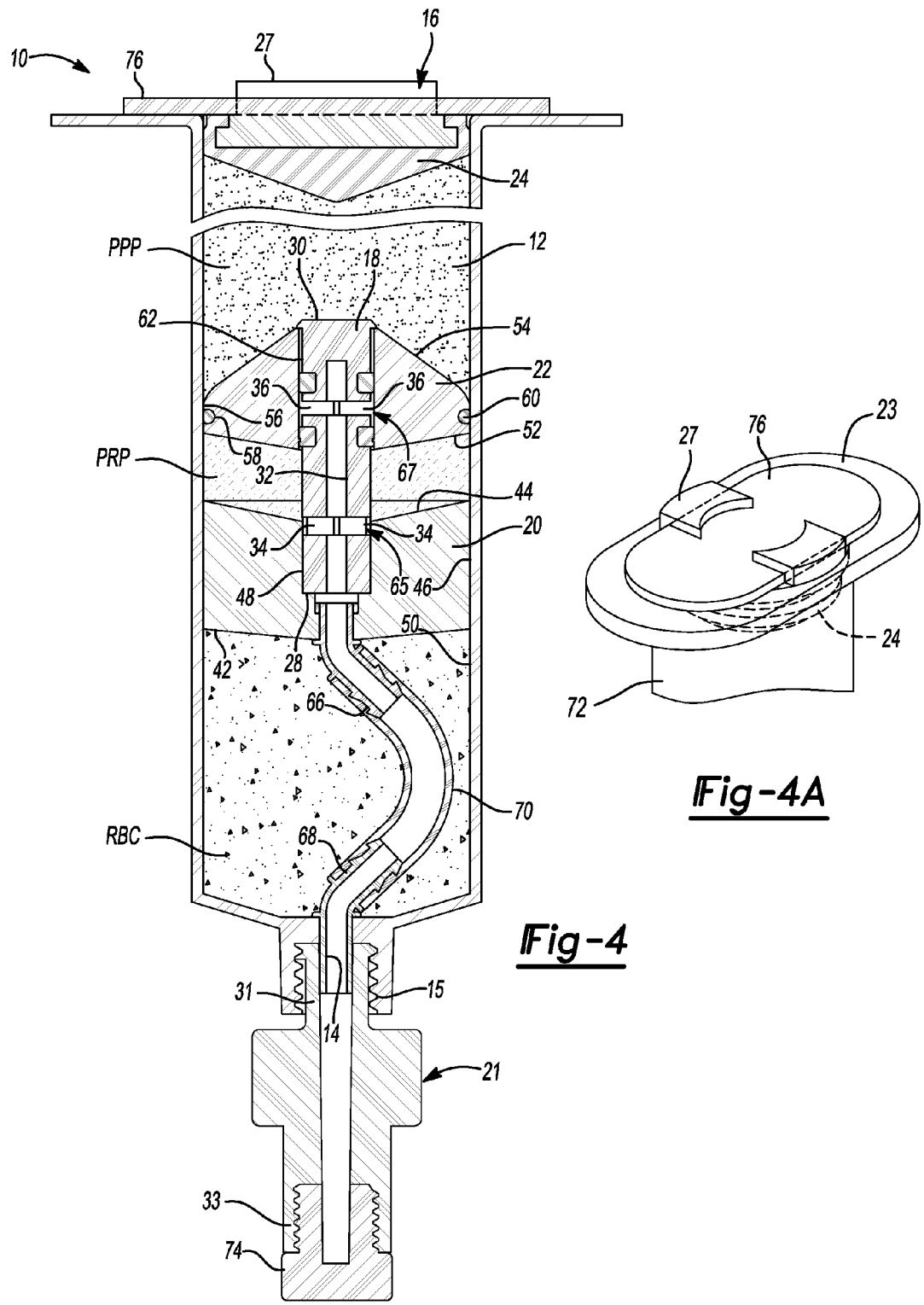

ALL-IN-ONE MEANS OF SEPARATING BLOOD COMPONENTS

CROSS-REFERENCE TO RELATED APPLICATION

This application is a divisional of U.S. patent application Ser. No. 12/417,789, U.S. Pat. No. 8,313,954, filed Apr. 3, 2009. The entire disclosure of each of the above references is incorporated by reference herein.

FIELD

The present disclosure relates to sterile devices, systems, and methods for separating components of a composition, such as blood.

BACKGROUND

The statements in this section merely provide background information related to the present disclosure and may not constitute prior art.

Whole blood includes a variety of different fractions or parts. For example, human whole blood includes platelet rich plasma (PRP), platelet poor plasma (PPP), red blood cells (RBCs), and white blood cells (WBCs). These different blood fractions have a variety of clinical and experimental uses. A typical blood separation device must be loaded with a separate syringe that contains whole blood drawn from a source, such as a patient's blood vessel. The separation device is then centrifuged and a different syringe is used to draw the separated components from the device for delivery to a desired area. The use of separate syringes to load and unload the separation device is cumbersome, time consuming, and not cost efficient. Further, the possibility of contamination increases each time blood is transferred.

Thus, there is a need for an all-in-one separation device, and method of use, that can be used to draw blood directly from a source, such as a patient, can be centrifuged to separate different fractions of the whole blood according to density, and can be used to deposit select fractions at an area of interest.

SUMMARY

The present teachings provide for a device having a separation chamber for separating components of a composition according to density. The device includes a port, a buoy guide post, a first buoy, a second buoy, a passage, a first valve, and a second valve. The port provides fluid communication between an interior and an exterior of the separation chamber. The first buoy is fixedly mounted to the buoy guide post and slidably mounted within the separation chamber. The second buoy is slidably mounted to the buoy guide post and movable between a first position and a second position along the buoy guide post. The passage is defined in the buoy guide post and is in fluid communication with the port. The first valve in the buoy guide post is in fluid communication with the passage and an area of the separation chamber between the first buoy and the second buoy. The second valve in the buoy guide post is in fluid communication with the passage and an area of the separation chamber between the second buoy and an end of the separation chamber that is opposite to the port. The second buoy closes the first valve and opens the second valve when in the first position. The second buoy opens the first valve and closes the second valve when in the second position. The second buoy has a density such that after spinning the device for a suitable period of time a first component of the composition is isolated between the first buoy and the second buoy and a second component of the composition is isolated between the second buoy and the end of the separation chamber that is opposite to the port.

The present teachings further provide for a method for separating whole blood into different components. The method includes the following: drawing the whole blood directly from a patient into a separation chamber through a port of the separation chamber, the separation chamber having a first buoy fixedly mounted to a buoy guide post and a second buoy slidably mounted to the buoy guide post, the buoy guide post having a first valve and a second valve, the first valve is closed and the second valve is open when the second buoy is in a first position, the whole blood is drawn into the separation chamber through the second valve into an area between the second buoy and a plunger slidably mounted in the separation chamber; rotating the chamber in a centrifuge for a sufficient period of time such that the second buoy moves to a second position in which the second buoy is spaced apart from the first buoy to close the second valve and open the first valve and the components of the whole blood separate according to density such that red blood cells are between the port and the first buoy, platelet rich plasma is between the first buoy an the second buoy, and platelet poor plasma is between the second buoy and the plunger; depressing the plunger to a first distance within the separation chamber to move the first buoy from the second position to the first position to force the platelet rich plasma through the first valve and out of the separation chamber through the port, to close the first valve, and to open the second valve; applying the platelet rich plasma directly to an area of interest through an applicator attached to the port; further depressing the plunger to a second distance within the separation chamber that is greater than the first distance to force the platelet poor plasma through the second valve and out of the separation chamber through the port; and applying the platelet poor plasma directly to an area of interest through an applicator attached to the port.

The present teachings also provide for a method for separating bone marrow aspirate into different components. The method includes: drawing the bone marrow aspirate directly from a patient into a separation chamber through a port of the separation chamber, the separation chamber having a first buoy fixedly mounted to a buoy guide post and a second buoy slidably mounted to the guide post, the buoy guide post having a first valve and a second valve, the first valve is closed and the second valve is open when the second buoy is in a first position, the bone marrow aspirate is drawn into the separation chamber through the second valve into an area between the second buoy and a plunger slidably mounted in the separation chamber; rotating the chamber in a centrifuge for a sufficient period of time such that the second buoy moves to a second position in which the second buoy is spaced apart from the first buoy to close the second valve and open the first valve and separate the components of the bone marrow aspirate according to density such that red blood cells are between the port and the first buoy, multipotent cells are between the first buoy an the second buoy, and bone marrow plasma is between the second buoy and the plunger; depressing the plunger to a first distance within the separation chamber to move the first buoy from the second position to the first position to force the multipotent cells through the first valve and out of the separation chamber through the port, to close the first valve, and to open the second valve; applying the multipotent cells directly to an area of interest through an applicator attached to the port; further depressing the plunger to a second distance within the separation chamber that is greater than the first distance to force the bone marrow plasma through the second valve and out of the separation chamber through the port; and applying the bone marrow plasma directly to an area of interest through an applicator attached to the port.

The present teachings also provide for a device having a separation chamber for separating components of a composition according to density that includes a port, a first buoy, and a second buoy. The port provides fluid communication between an interior and an exterior of the separation chamber. The first buoy is slidably mounted within the separation chamber. The second buoy is slidably mounted within the separation chamber. The second buoy has a density such that after spinning the device for a suitable period of time a first component of the composition is isolated between the first buoy and the second buoy and a second component of the composition is isolated between the second buoy and an end of the separation chamber that is opposite to the port.

The present teachings further provide for a method for separating whole blood into different components. The method includes: drawing the whole blood directly from a patient into a separation chamber through a port, the separation chamber having a first buoy slidably mounted in the separation chamber and a second buoy slidably mounted in the separation chamber, the whole blood is drawn into the separation chamber into an area between the second buoy and a plunger slidably mounted in the separation chamber; rotating the chamber in a centrifuge for a sufficient period of time such that the second buoy moves to a second position in which the second buoy is spaced apart from the first buoy and the components of the whole blood separate according to density such that red blood cells are between the port and the first buoy, platelet rich plasma is between the first buoy an the second buoy, and platelet poor plasma is between the second buoy and the plunger; depressing the plunger to a first distance within the separation chamber to move the first buoy from the second position to the first position to force the platelet rich plasma out of the separation chamber through the port; applying the platelet rich plasma directly to an area of interest through an applicator attached to the port; further depressing the plunger to a second distance within the separation chamber that is greater than the first distance to force the platelet poor plasma out of the separation chamber through the port; and applying the platelet poor plasma directly to an area of interest through the applicator attached to the port.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

Figure 1A:
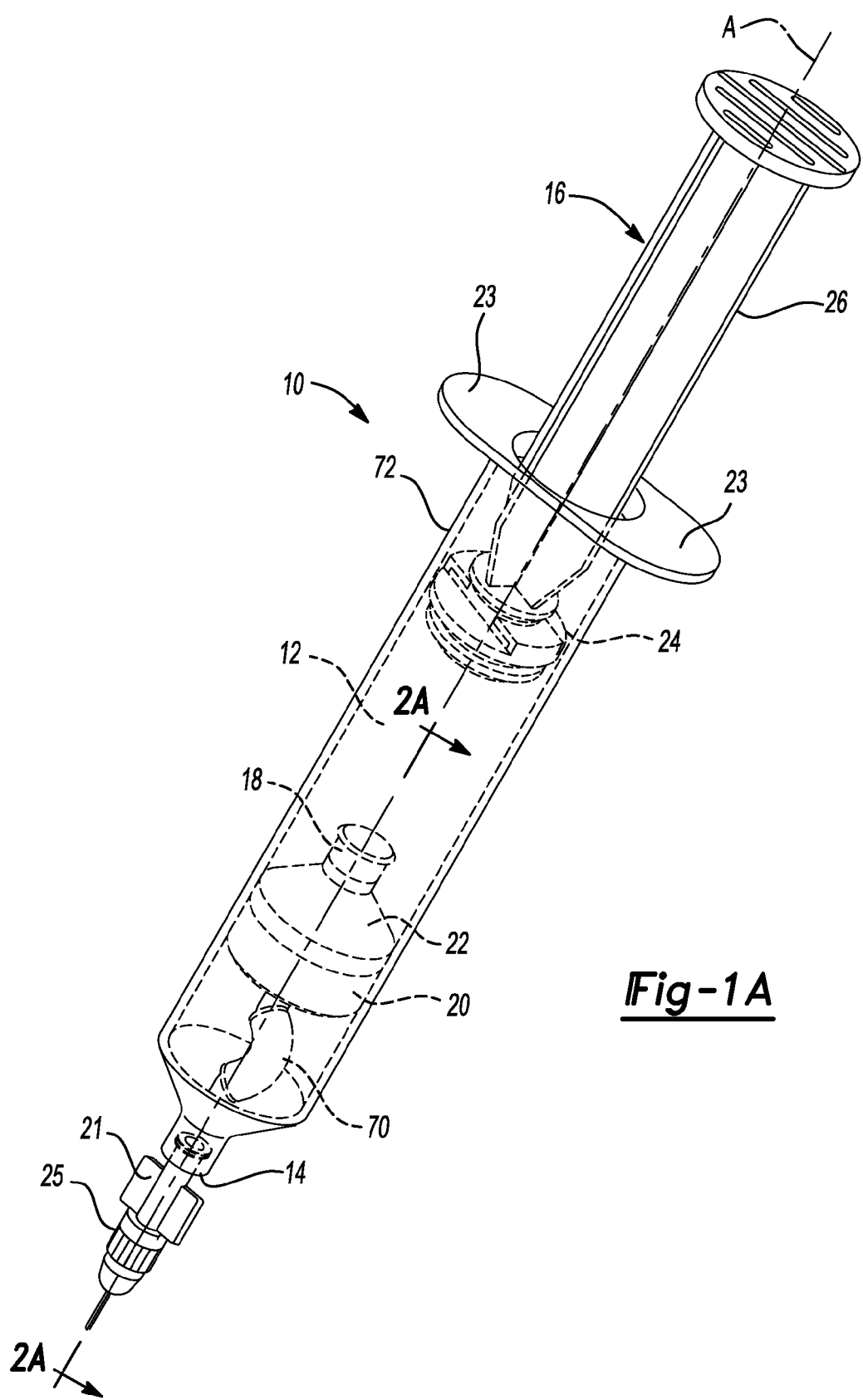
FIG. 1A is a perspective view of a device for separating components of a multi-component composition according to the present teachings.
Figure 5:
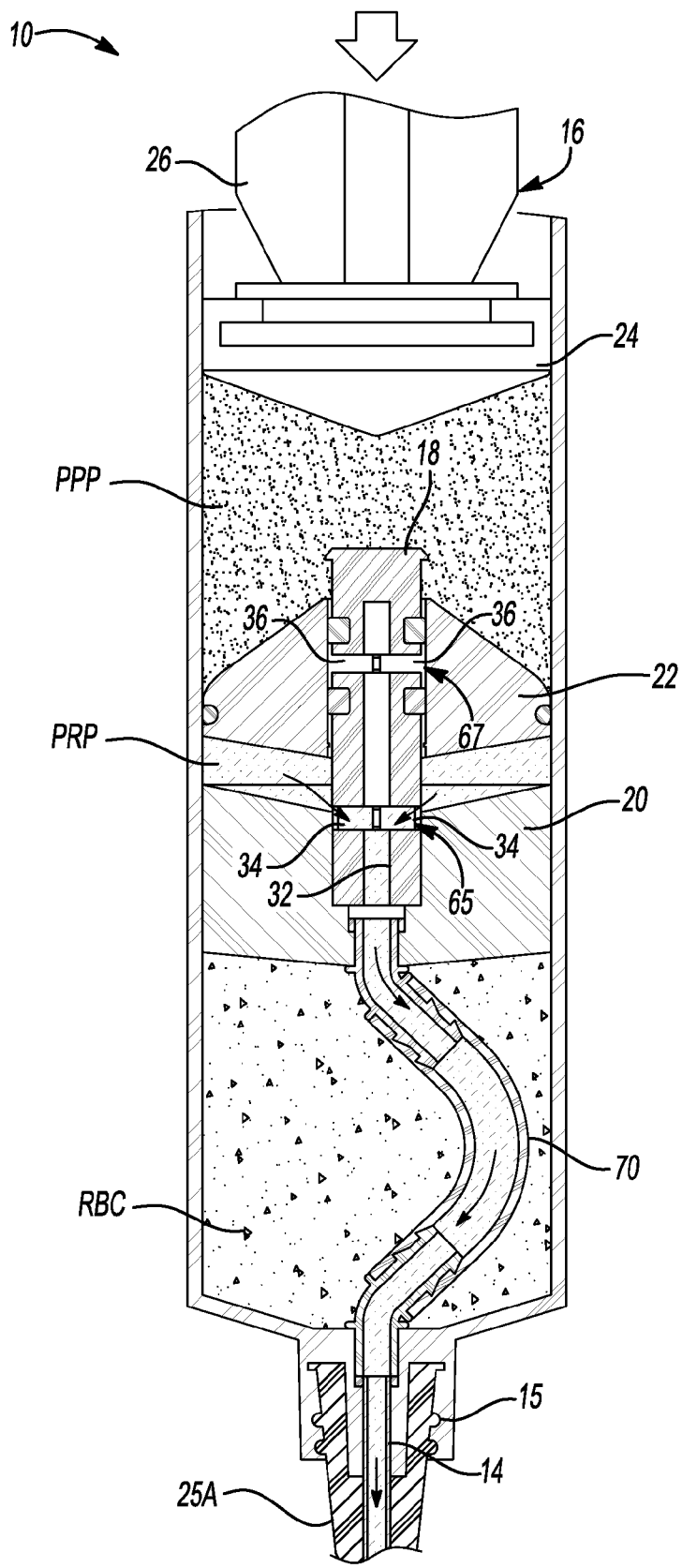
Figure 6:
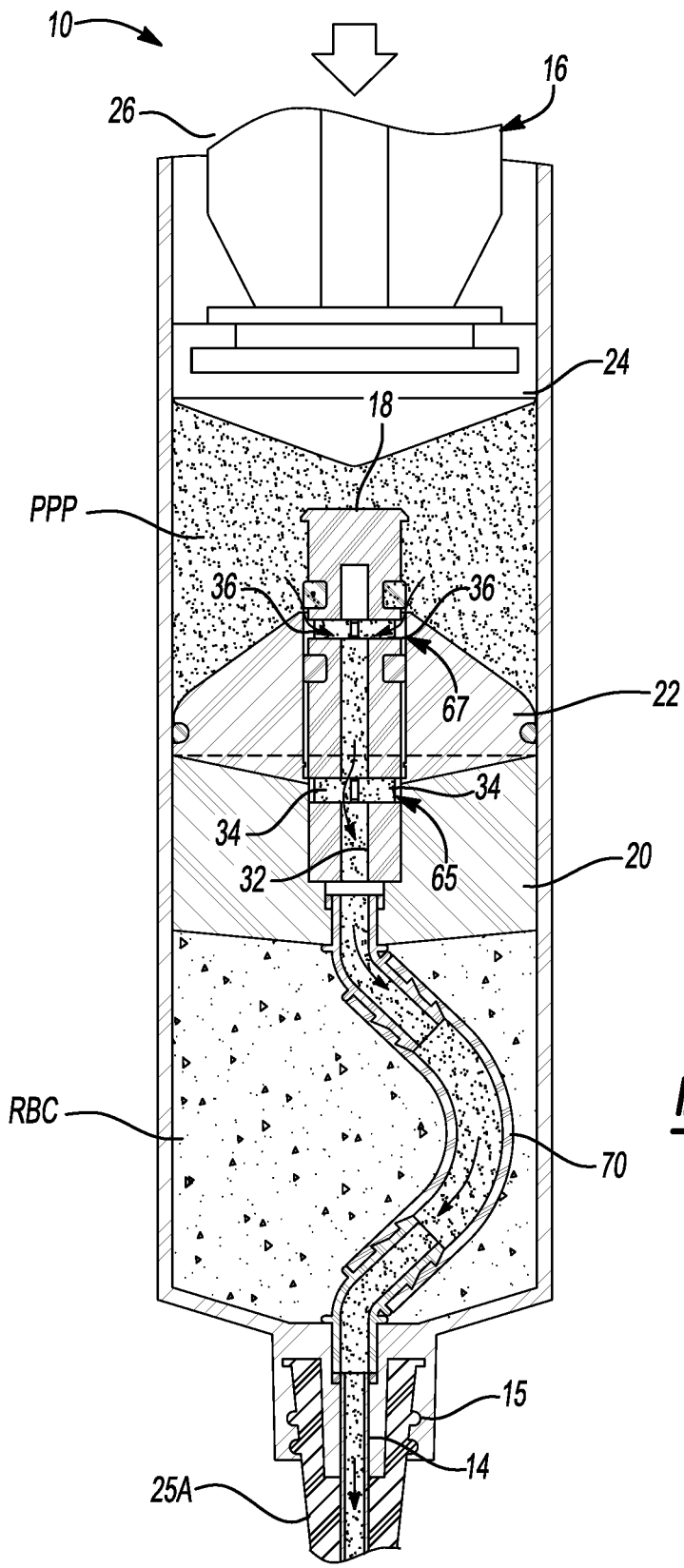

FIG. 4 is a cross-sectional view of the device of FIG. 1A, the device having been loaded with whole blood and spun for a suitable period of time to separate different components of whole blood according to density, platelet poor plasma being between a second buoy and a plunger base, platelet rich plasma being between the second buoy and a first buoy, and red blood cells being between the first buoy and an inlet/outlet port;

FIG. 4A is a top perspective view of the device as illustrated in FIG. 4 with the plunger base secured at a distal end of the device with a locking tab;

FIG. 5 is a cross-sectional view of the device of FIG. 1A showing the plunger being actuated to expel the platelet rich plasma from the device; and FIG. 6 is a cross-sectional view of the device of FIG. 1A showing the plunger being actuated further to expel the platelet poor plasma from the device.

DETAILED DESCRIPTION

The following description is merely exemplary in nature and is not intended to limit the present disclosure, application, or uses.

With initial reference to FIGS. 1A, 1B, 2A, and 2B, a device for separating components of a multi-component composition according to the present teachings is illustrated at reference numeral 10. The device 10 is an all-in-one device that can be used to extract the multi-component composition directly from a source, such as a patient, can be centrifuged to separate different components of the composition according to density, and can be used to deposit select components of the composition directly at an area of interest, such as a wound site.

The device 10 generally includes a separation chamber 12, a port 14 for drawing the multi-component composition into the separation chamber 12 and for dispensing the separated components from the separation chamber 12, a plunger 16, and a buoy guide post 18 to which are mounted a first buoy 20 and a second buoy 22.

The separation chamber 12 can take the form of any suitable container having any suitable size or shape. For example and as illustrated throughout the figures, the separation chamber 12 can be cylindrical and can form the body of a syringe. The separation chamber 12 includes a longitudinal axis A.

The plunger 16 is slidably mounted within the separation chamber 12. In particular, the plunger 16 includes a plunger base 24 and a plunger handle 26. The plunger base 24 is seated within the separation chamber 12 and the plunger handle 26 extends from the plunger base 24 and from the separation chamber 12.

Figure 1B:
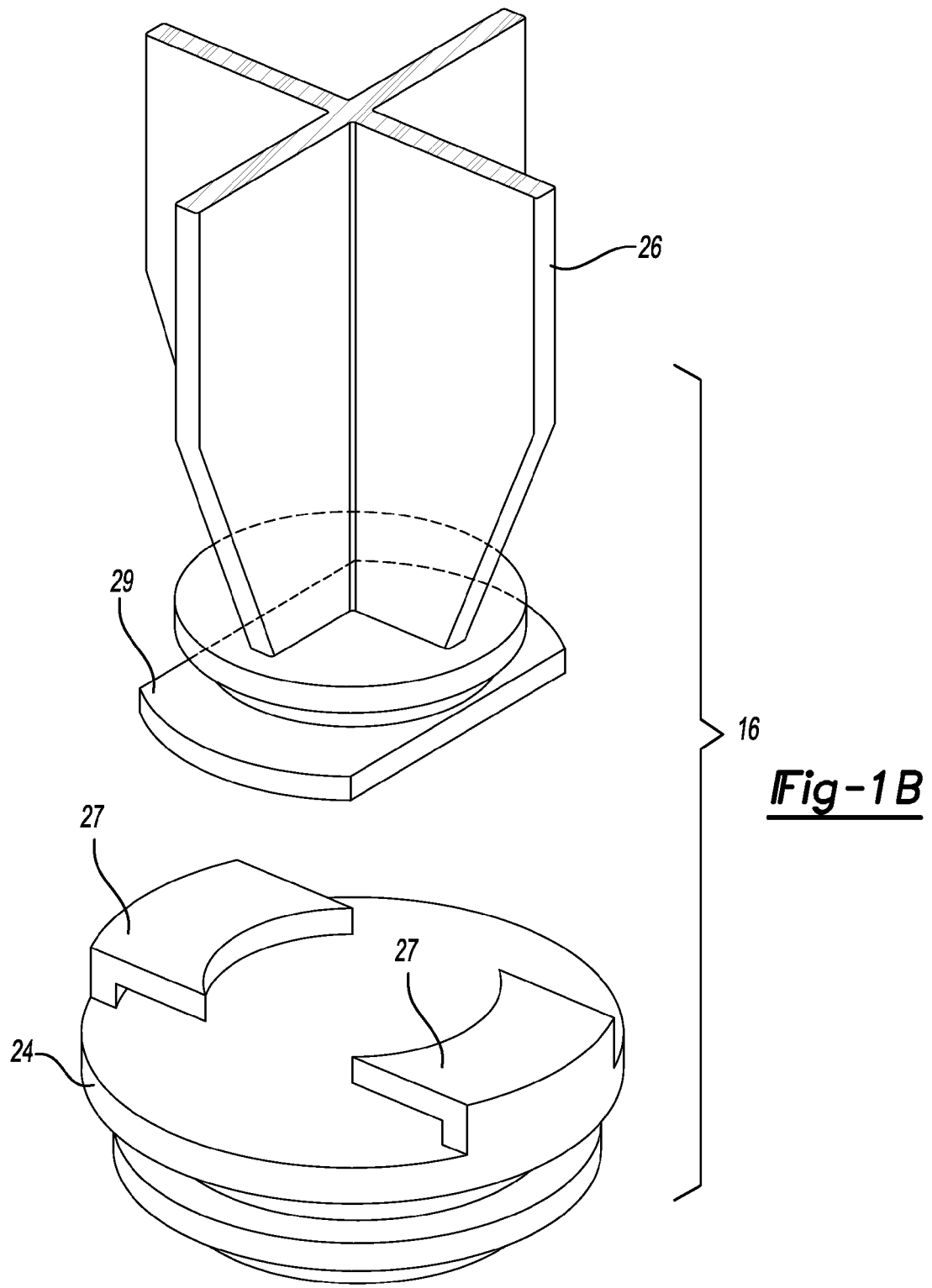
FIG. 1B is an exploded view of a plunger of the device of FIG. 1A.

The plunger handle 26 can be removably attached to the base 24 in any suitable manner. For example and as illustrated in FIG. 1B, the plunger base 24 can include two opposing locking flanges 27 that extend from an upper surface of the base 24. The plunger handle 26 can include a locking tab 29 that mates with the flanges 27 upon placing the locking tab 29 between the flanges 27 and rotating the plunger handle 26 90° such that the locking tab 29 is under the flanges 27 and between the flanges 27 and the remainder of the base 24. The plunger 16 facilitates drawing of the multi-component composition into the separation chamber 12 by creating a vacuum therein and facilitates dispensing of the separated components therefrom, as further described herein. Syringe handles 23 extend from an exterior surface of the separation chamber 12 to facilitate operation and handling of the device 10.

The multi-component composition to be separated is drawn into, and dispensed from, the separation chamber 12 through the port 14. The port 14 can be any suitable through port that permits the passage of the multi-component composition to be separated, such as whole blood. For example, the port 14 can include a Luer lock 15. The port 14 can cooperate with a variety of devices, such as, for example, an extension nozzle 21 (FIG. 1).

The extension nozzle 21 can be any suitable connector, such as a Luer extension as illustrated. The nozzle 21 includes a first Luer lock connector 31 at a first end and a second Luer lock connector 33 at a second end. The first Luer lock 31 cooperates with the Luer lock 15 of the port 14. The second Luer lock 33 cooperates with a needle tip 25 (FIG. 1) or a spray tip (not shown). The second Luer lock 33 can be a Luer activated type valve that closes when the needle tip 25 is detached. As further described herein, the nozzle 21 facilitates use of the port 14 as both a draw port and expulsion port while maintaining sterility of the device 10.

The needle tip 25 is used to draw the composition into the separation chamber 12. Both the needle tip 25 and the spray tip facilitate application of various components of the composition to a delivery site, such as a wound site.

Figure 3A:
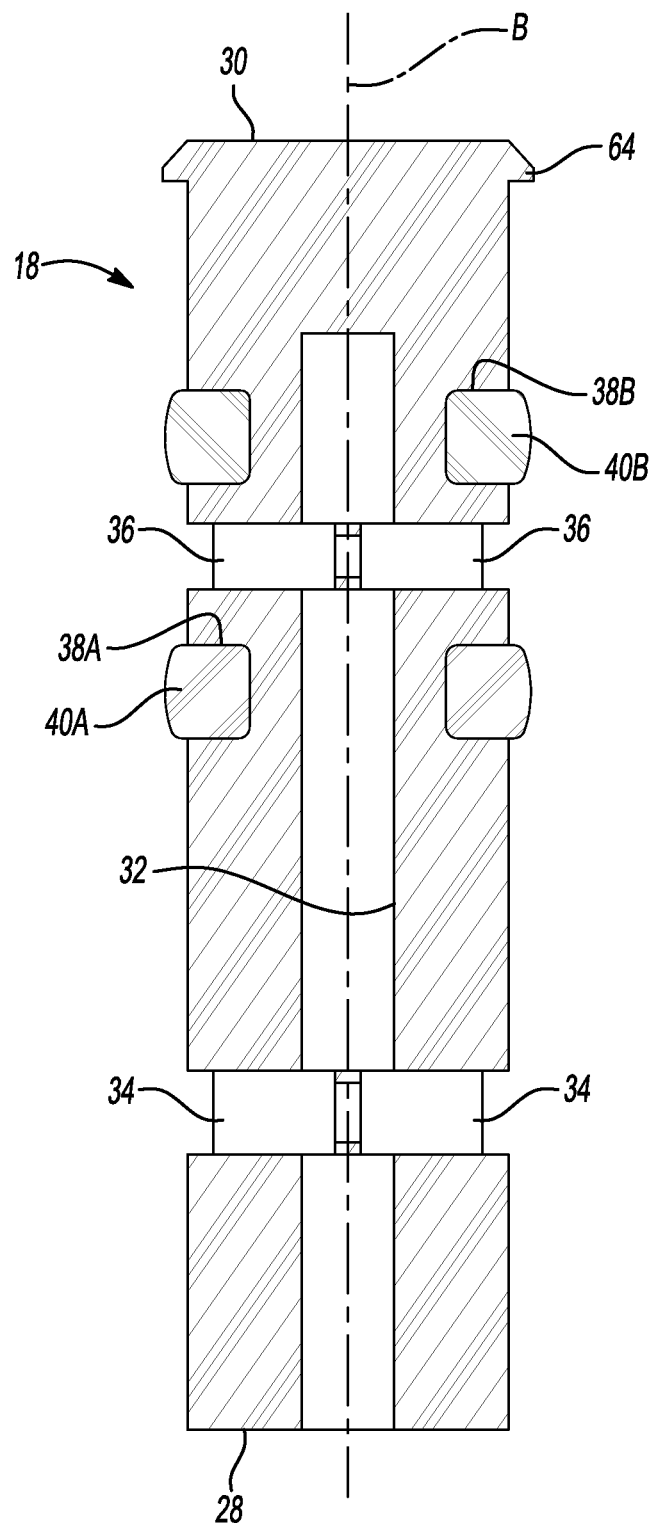
FIG. 3A is a cross-sectional view of a buoy guide post of the device of FIG. 1A.
Figure 3B:
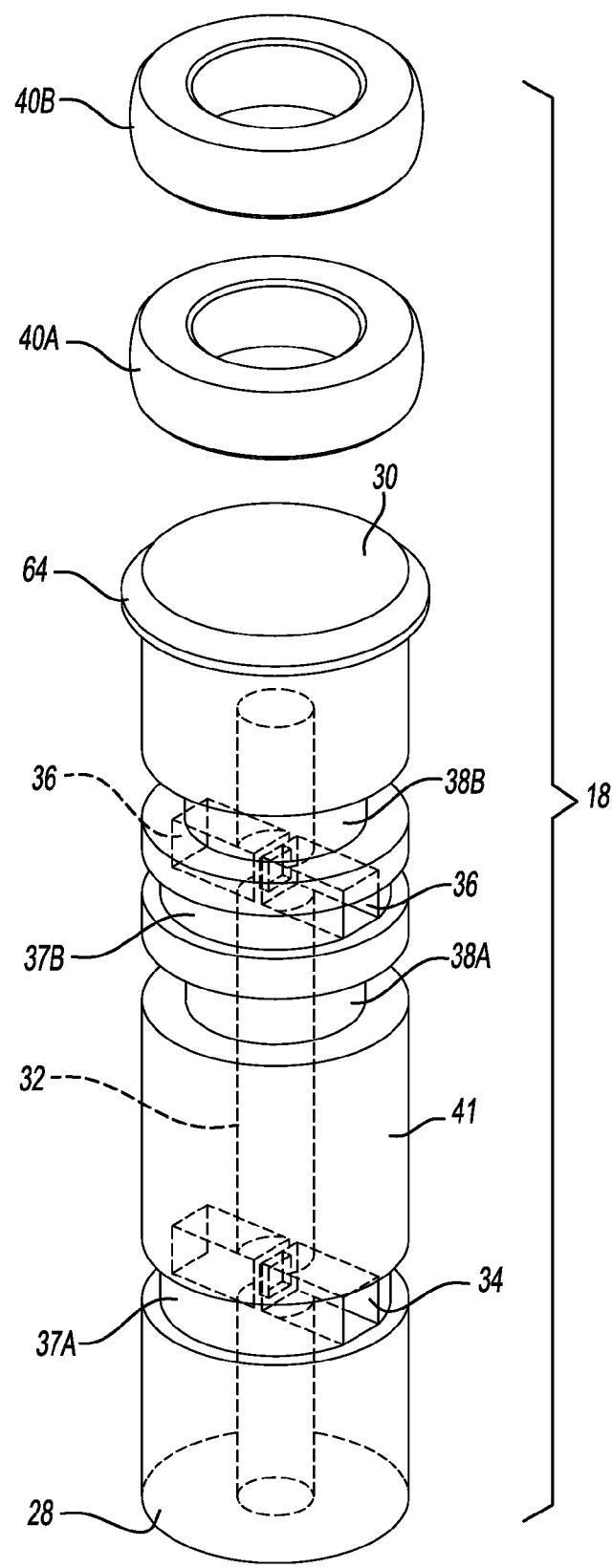
FIG. 3B is an exploded perspective view of the buoy guide post of FIG. 3A.

With additional reference to FIGS. 3A and 3B, the buoy guide post 18 includes a first end 28 and a second end 30 that is opposite to the first end 28. The buoy guide post 18 has a generally cylindrical shape. The guide post 18 defines a center passage or channel 32. The channel 32 extends from the first end 28 along a longitudinal axis B of the guide post 18. As illustrated, the channel 32 extends from the first end 28 and terminates just prior to reaching the second end 30.

Figure 3C:
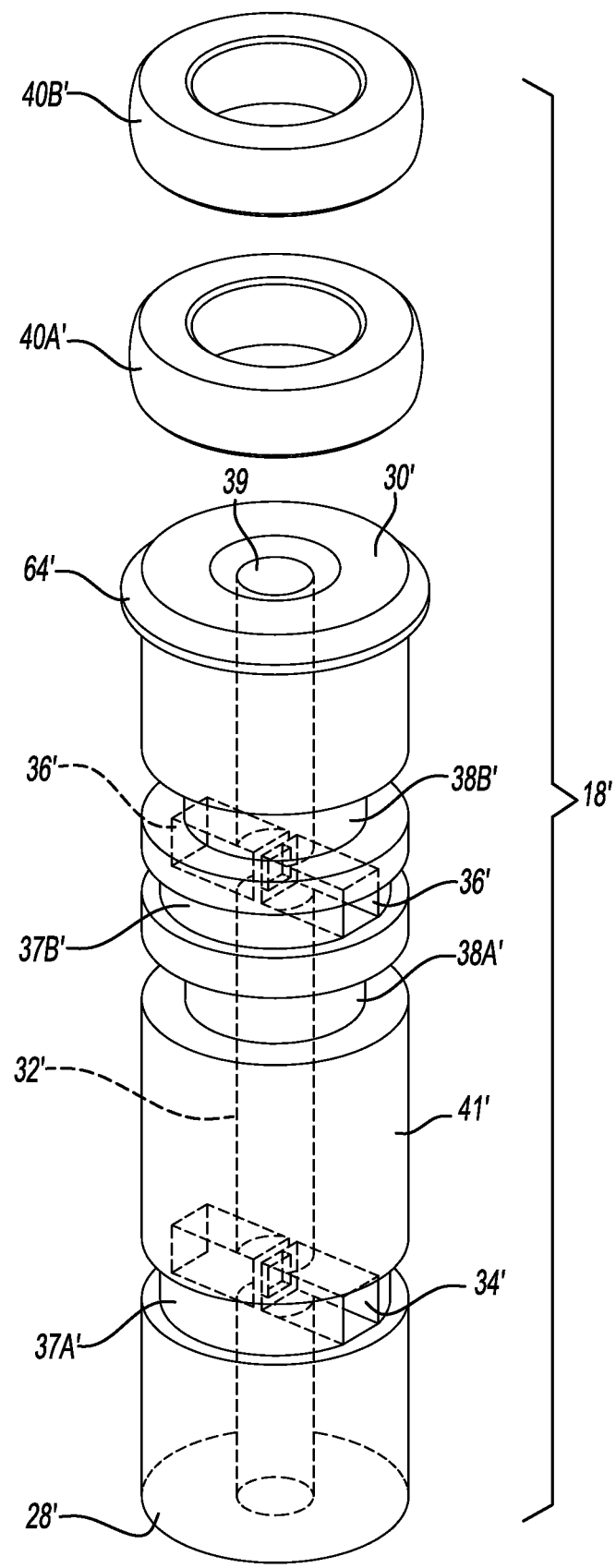
FIG. 3C is an exploded perspective view of an additional buoy guide post that may be used with the device of FIG. 1A.

With additional reference to FIG. 3C, an additional buoy guide post according to the present teachings is illustrated at reference number 18'. Features of the buoy guide post 18' that are also included in the guide post 18 are designated with the same reference numbers, but include the prime (') symbol. The description of the common features set forth herein with respect to the guide post 18 also applies to the guide post 18'. The primary difference between the guide post 18 and the guide post 18' is that the channel 32' extends to the second end 30' to provide a conduit that extends completely through the buoy guide post 18' from the first end 28' to the second end 30'.

The guide post 18 further includes at least one first aperture 34 and at least one second aperture 36. The first aperture 34 is proximate to the first end 28 and the second aperture 36 is proximate to the second end 30. As illustrated, the guide post 18 includes two first apertures 34 and two second apertures 36. The two first apertures 34 and the two second apertures 36 are positioned at a 180° interval about an outer circumference of the guide post 18. Openings of each of the first apertures 34 and each of the second apertures 36 are located in annular recesses 37A and 37B respectively.

The first apertures 34 and the second apertures 36 each provide fluid communication between the channel 32 and the separation chamber 12. As illustrated in FIG. 3C, the guide post 18' includes a third aperture 39 at the second end 30'. The third aperture 39 facilitates fluid communication between the channel 32' and the separation chamber 12'.

On opposite sides of, and proximate to, the second aperture 36 are annular recesses 38A and 38B within the guide post 18. The annular recesses 38A and 38B each accommodate an o-ring 40A and 40B, respectively. As further described herein, the o-rings 40A and 40B facilitate movement of the second buoy 22 along the longitudinal axis B of the buoy guide post 18 between the first end 28 and the second end 30 and restrict passage of the composition past the o-rings 40A and 40B. The o-rings 40A and 40B can be made of any suitable material, such as a polymeric material. The buoy guide post 18 is positioned within the separation chamber 12 such that the longitudinal axis B of the guide post 18 extends along the longitudinal axis A of the separation chamber 12.

The first buoy 20 is generally shaped as a right cylinder. With additional reference to FIG. 4, the first buoy 20 includes a lower or first surface 42 and an upper or second surface 44 that is opposite to the lower surface 42. Extending between an outer circumference of the lower surface 42 and an outer circumference of the upper surface 44 is a circular sidewall 46. The upper surface 44 has a hemi-spherical shape and is concave with respect to the remainder of the first buoy 20. The lower surface 42 has a hemi-spherical shape and is convex with respect to the remainder of the first buoy 20.

A through bore 48 extends through an axial center of the first buoy 20. The buoy guide post 18 is positioned within the through bore 48 and is fixedly mounted thereto in any suitable manner, such as with a press-fit as illustrated or with a suitable adhesive. The buoy guide post 18 is mounted to the first buoy 20 such that the first end 28 of the guide post 18 is seated within the first buoy 20 proximate to the lower surface 42 with the first aperture 34 at the upper surface 44. In particular, the guide post 18 is positioned such that a majority of the first aperture 34 is recessed within the through bore 48 of the first buoy 20 with only a small portion of the first aperture 34 being slightly above the upper surface 44 at the center of the first buoy 20. Further, the first aperture 34 is spaced apart from the first buoy 20 as a result of being positioned within the recess 37A. Thus, there is a slight clearance between the first aperture 34 and the second buoy 22 through which the multi-component composition can pass to provide fluid communication between the first aperture and the area between the first buoy 20 and the second buoy 22. Because the upper surface 44 is concave, the first aperture 34 is recessed below, and does not pass across, a plane that extends completely across the upper surface 44 and is perpendicular to the sidewall 46.

The first buoy 20 is positioned within the separation chamber 12 such that the lower surface 42 faces the port 14 and the upper surface 44 faces the plunger 16. The circular sidewall 46 of the first buoy 20 faces an inner sidewall 50 of the separation chamber 12. When the device 10 is not being rotated or spun, the sidewall 46 contacts the inner sidewall 50 of the separation chamber 12 to restrict the passage of the multi-component composition being separated between the sidewall 46 and the inner sidewall 50.

The second buoy 22 is generally shaped as a right cone. The second buoy 22 includes a lower or first surface 52 and an upper or second surface 54 that is opposite to the lower surface 52. Extending between the lower surface 52 and the upper surface 54, around an outer periphery of the second buoy 22, is a cylindrical sidewall 56. The upper surface 54 slopes downward toward the sidewall 56. The lower surface 52 has a hemi-spherical shape and is convex with respect to the remainder of the second buoy 22. The sidewall 56 includes an annular recess 58 that extends around the sidewall 56. The annular recess 58 accommodates an o-ring 60 that extends around the cylindrical sidewall 56 of the second buoy 22. When the device 10 is not being rotated or spun, the sidewall 56 contacts the inner sidewall 50 of the separation chamber 12 to restrict the passage of the multi-component composition being separated between the sidewall 56 and the inner sidewall 50. The o-ring 60 can be made of any suitable material that facilitates movement of the second buoy 22 within the separation chamber 12 and restricts passage of the composition between the sidewall 56 and the inner sidewall 50. For example, the o-ring 60 can be made of a suitable polymeric material.

A through bore 62 extends through the center of the second buoy 22. The buoy guide post 18 is positioned within the through bore 62. The second buoy 22 is slidably mounted to the guide post 18 to allow the second buoy 22 to slidably move along the longitudinal axis A of the separation chamber 12 and the longitudinal axis B of the through bore 48. The second buoy 22 is seated on the o-rings 40A and 40B, which facilitate movement of the second buoy 22 and restricts the flow of the multi-component composition past the o-rings 40A and 40B. The second buoy 22 is slightly spaced apart from an outer surface 41 of the buoy guide post 18 due to the presence of the o-rings 40A and 40B.

The second buoy 22 can slidably move between a first position (FIGS. 2A and 2B) in which the second buoy 22 contacts the first buoy 20 and a second position (FIG. 4) in which the second buoy 22 is spaced apart from the first buoy 20. In the first position, the lower surface 52 of the second buoy 22 is flush with the upper surface 44 of the first buoy 20 to restrict passage of the multi-component composition through the first aperture 34 and into the separation chamber 12. When the second buoy 22 is in the first position, there is a passageway between the second aperture 36 and the separation chamber 12 to provide fluid communication between the channel 32 of the guide post 18 and the portion of the separation chamber 12 that is between the second buoy 22 and the plunger 16. The passageway is provided due to the clearance between the second buoy 22 and both the second aperture 36 and the o-ring 40B In the second position, the second buoy 22 is spaced apart from the first buoy 20 and is proximate to the second end 30 of the guide post 18. The guide post 18 includes an annular tab 64 (FIG. 3A) at the second end 30 to prevent the second buoy 22 from sliding off of the guide post 18. With the second buoy 22 spaced apart from the first buoy 20, the clearance between the first aperture 34 and the first buoy 20 permits fluid communication between the channel 32 of the guide post 18 and the portion of the separation chamber 12 between the first buoy 20 and the second buoy 22. In the second position, the second buoy 22 mates with the o-ring 40B to obstruct the passageway between the second aperture 36 and the separation chamber 12 and to restrict fluid communication between the second aperture 36 and the area of the separation chamber 12 above the second buoy 22.

Thus, the first aperture 34 provides a first valve 65 and the second aperture 36 provides a second valve 67 between the separation chamber 12 and the channel 32 of the buoy guide post 18, which is in ultimate fluid communication with the port 14. Passage of the composition through the first and second apertures 34 and 36 is controlled by the position of the second buoy 22. When the second buoy 22 is in the first position, the second buoy 22 does not obstruct the flow of the composition through the second aperture 36, thus opening the second valve 67 between the channel 32 and the area of the separation chamber 12 above the second buoy 22. In the first position, the second buoy 22 restricts flow of the composition through the first aperture 34 and into the separation chamber 12, thus closing the first valve 65 between the channel 32 and the area of the separation chamber 12 between the first buoy 20 and the second buoy 22.

When the second buoy 22 is in the second position, the second buoy 22 obstructs the flow of the composition through the second aperture 36, thus closing the second valve 67 between the channel 32 and the area of the separation chamber 12 above the second buoy 22. In the second position, the second buoy 22 does not restrict passage of the composition through the first aperture 34, thus opening the first valve 65 between the channel 32 and the area of the separation chamber 12 between the first buoy 20 and the second buoy 22.

The first and the second buoys 20 and 22 can be made of any suitable material that will permit the buoys 20 and 22 to, upon rotating or spinning the device 10 in a centrifuge for a suitable period of time, move within the separation chamber 12 and settle between different components of the multi-component composition to be isolated. For example, when the device 10 is used for separating the components of whole blood, the buoys 20 and 22 can be made of a suitable high-density polyethylene material (HDPE). The HDPE of the buoys 20 and 22 will have a density that will permit separation of the whole blood such that red blood cells (RBCs) are between the port 14 and the first buoy 20; platelet rich plasma, buffy coat, or cell rich fractions (collectively "PRP") are between the first buoy 20 and the second buoy 22 when the second buoy 22 is in the second position; and platelet poor plasma (PPP) is between the second buoy 22 and the plunger base 24.

The first buoy 20 is provided with a greater density than the second buoy 22. In particular, the first buoy 20 can have a density of between about 1.070 g/ml and about 1.095 g/ml, such as 1.075 g/ml. The second buoy 22 can have a density between about 0.93 g/ml and about 0.955 g/ml, such as 0.945 g/ml. The assembly including the first buoy 20, the second buoy 22, and the buoy guide post 18 can have an overall density of between about 1.02 g/ml and about 1.09 g/ml, such as 1.045 g/ml.

Mounted at the lower surface 42 of the first buoy 20 is a first connector 66. The first connector 66 is in fluid communication with the channel 32 and extends beyond the lower surface 42 of the first buoy 20. Mounted to the port 14 is a second connector 68. The second connector 68 extends from the port 14 to within the separation chamber 12. A flexible tube or conduit 70 is connected to the first connector 66 and the second connector 68 to provide fluid communication between the port 14 and the buoy guide post 18.

The device 10 can be used to separate most any liquid composition into its constituent components by density. With particular reference to FIGS. 2 and 4-6, operation of the device 10 to separate RBCs, PPP and PRP from whole blood is described below.

Figure 2A:
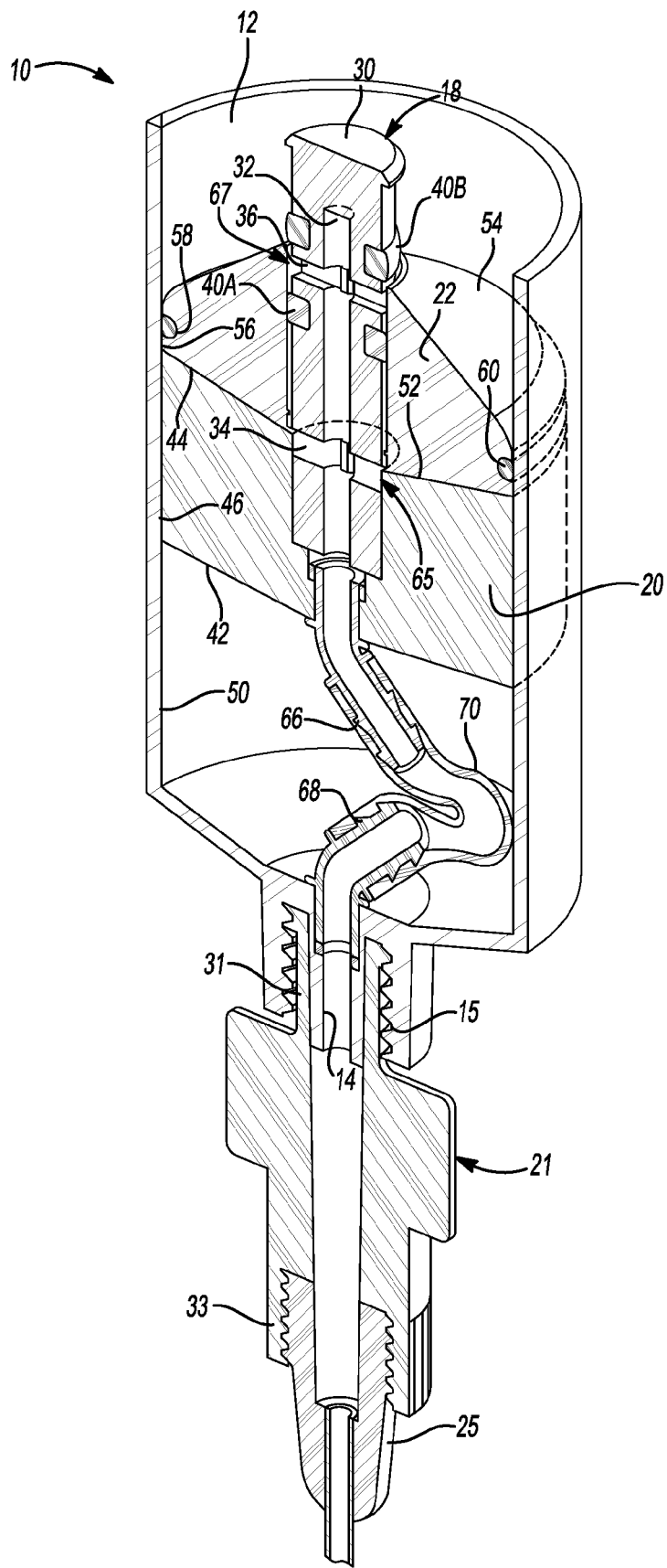
FIG. 2A is a perspective cross-sectional view of the device of FIG. 1A taken along line 2A-2A of FIG. 1A.
Figure 2B:
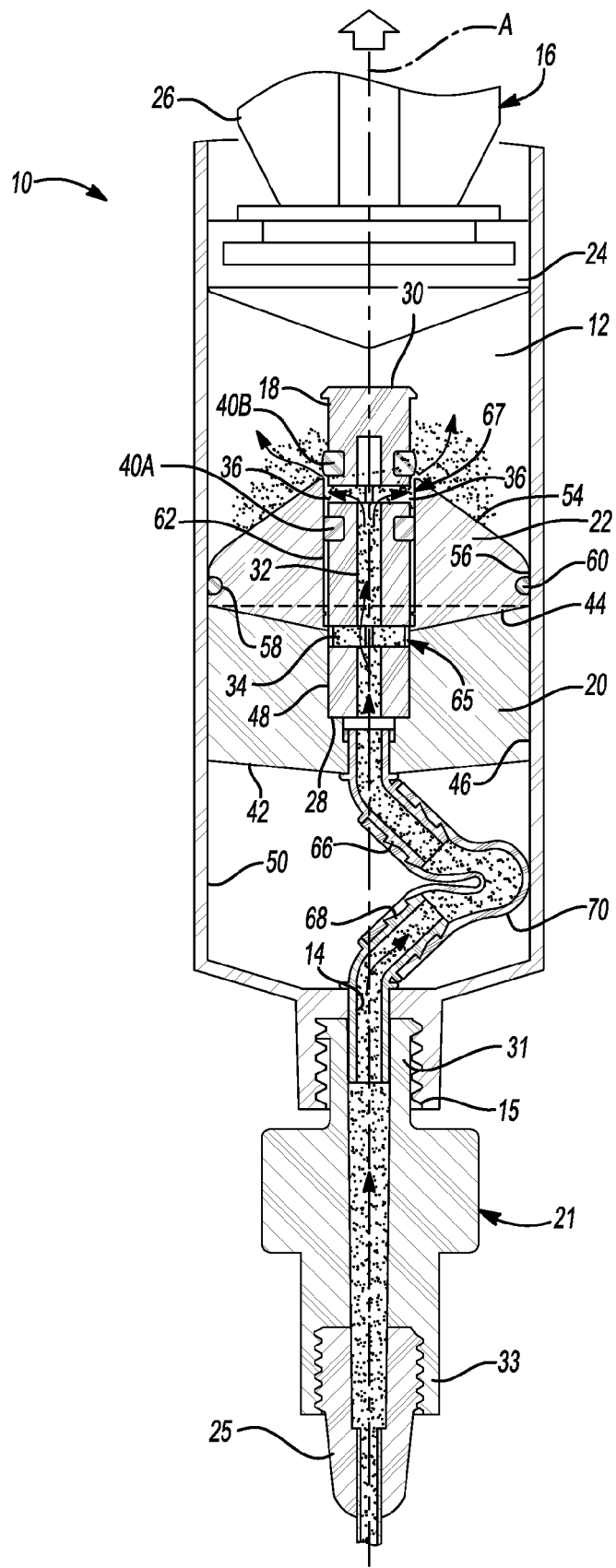
FIG. 2B is a cross-sectional view of the device of FIG. 1A.

Whole blood is loaded into the separation chamber 12 of the device 10 with the first buoy 20 proximate to the port 14 and the second buoy 22 in the first position, as illustrated in FIGS. 2A and 2B. In the first position, the second buoy 22 is in contact with the first buoy 20 to obstruct passage of blood into the separation chamber 12 through the first aperture 34, thereby closing the first valve 65 defined by the first aperture 34, and to permit the passage of blood into the separation chamber 12 through the second aperture 36, thereby opening the second valve 67 defined by the second aperture 36. Prior to loading, the plunger 16 is positioned such that the plunger base 24 is seated deep within the separation chamber 12 and is distal to an end 72 (FIG. 1) of the separation chamber 12 that is opposite to the port 14.

With the first Luer lock 31 of the extension nozzle 21 coupled to the Luer lock 15 of the port 14 and the needle tip 25 coupled to the second Luer lock 33 of the extension nozzle 21, the needle tip 25 is inserted into a source of whole blood, such as a blood vessel of a patient. The plunger 16 is then pulled outward to move the plunger base 24 toward the end 72 of the chamber 12. As illustrated in FIG. 2B, withdrawing the plunger 16 creates a vacuum in the separation chamber 12 that draws the whole blood through the port 14, the tube 70, the channel 32 of the guide post 18, the second aperture 36, and into the separation chamber 12 between the second buoy 22 and the plunger base 24.

Any suitable amount of whole blood can be drawn, such as 30 ml or 60 ml for example. The size of the separation chamber will vary depending on the amount of whole blood to be separated. For example, if 30 ml of whole blood is to be separated, then the separation chamber 12 can be sized to hold about 51 ml of fluid. If 60 ml of whole blood is to be separated, then the separation chamber 12 can be sized to hold about 94 ml of fluid. The diameter of the first and the second buoys 20 and 22 can be modified to fit chambers 12 of different diameters. The density of the buoys 20 and 22 can remain the same regardless of the diameters of the first and the second buoys.

After the blood is loaded into the separation chamber 12, the plunger handle 26 can be removed from the plunger base 24 by rotating the plunger handle 26 90° so that the locking tab 29 no longer engages the flanges 27 and the needle tip 25 can be removed from the second Luer lock connector 33 of the nozzle 21. If the Luer lock connector 33 is a Luer valve it will close upon removal of the needle tip 25. The Luer lock connector 33 can also be closed with a suitable sterile cover 74 (FIG. 4).

To prevent the plunger base 24 from moving and applying pressure on the whole blood in the chamber 12 as the device 10 is spun, the plunger base 24 can be provided with a density that is less than blood. A suitable locking device can also be used to secure the plunger base 24. For example and as illustrated in FIGS. 4 and 4A, with the plunger base 24 positioned generally co-planar with the syringe handles 23, a locking tab 76 can be inserted beneath the locking flanges 27 so that it rests on the syringe handles 23 and restricts movement of the plunger base 24.

With the whole blood seated between the second buoy 22 and the plunger base 24, the device 10 is ready to be spun to separate the components of whole blood according to density. The device 10 is spun using a suitable rotational device, such as a centrifuge.

The device 10 can be spun for any suitable period of time to separate the different components of blood. For example, the device 10 can be spun for about 12 to about 15 minutes at about 3,200 rpm. As the device 10 spins, the inner sidewall 50 of the separation chamber 12 flexes or expands outward from the longitudinal axis A of the separation chamber 12 to provide a clearance between the sidewall 46 of the first buoy 20 and the inner sidewall 50, as well as between the sidewall 56 of the second buoy 22 and the inner sidewall 50 to allow the first and the second buoys 20 and 22 to move within the separation chamber 12 and allow the whole blood to move past the first and the second buoys 20 and 22.

As the device 10 is rotated, the different blood components separate according to density. Further, the first and second buoys 20 and 22 slidably move along the longitudinal axis A of the separation chamber 12 until the buoys reach a position where the density of each of the buoys 20 and 22 is proximate to, or matches, the density of surrounding blood components. In particular and as illustrated in FIG. 4, the first buoy 20 moves away from the port 14 to a position between the RBCs and the PRP. The second buoy 22 moves to the second position such that the second buoy 22 is spaced apart from the first buoy 20 with the PRP between the first buoy 20 and the second buoy 22. The PPP settles between the second buoy 22 and the plunger base 24. In the second position, the second buoy 22 opens the first valve 65 between the separation chamber 12 and the channel 32 defined by the first aperture 34 and closes the second valve 67 defined by the second aperture 36.

To withdraw the different blood components from the separation chamber 12, the device 10 is removed from the rotational device, the plunger handle 26 is reattached to the plunger base 24, the extension nozzle 21 is removed, and a suitable applicator, such as a spray tip or a new sterile needle tip 25A, is coupled directly to the Luer lock 15 of the port 14. Thus, the port 14 is both an intake port and an expulsion port.

To maintain sterility of the port 14, the device is packaged with the extension nozzle 21 attached to the port 14. The port 14 is shielded from the environment until after centrifugation when the extension nozzle 21 is removed. Thus, the port 14 is only exposed to the environment once, which enhances the sterility of the port 14.

As illustrated in FIG. 5, the plunger 16 is pushed into the separation chamber 12 to exert pressure on the PPP and the second buoy 22. The second buoy 22 is pushed back toward the first buoy 20 and to the first position. The presence of the o-ring 60 prevents passage of the PPP around the second buoy 22 as pressure is exerted on the PPP by the plunger 16. The o-ring 60 also facilitates movement of the second buoy 22 in response to activation of the plunger 16.

As the gap between the second buoy 22 and the first buoy 20 is closed, the PRP between the first buoy 20 and the second buoy 22 is forced through the first valve 65 defined by the first aperture 34. The PRP moves through the first aperture 34, the channel 32, and the flexible tube 70 to the port 14. From the port 14 the PRP is expelled from the device 10 through the needle tip 25A to a desired area.

The isolated PRP can be used for general wound healing and to facilitate the completion of most any orthopaedic procedure. More specifically, PRP can be used to treat bone fractures, non-unions, bony defects, tendinitis, and plantar fasciitis. PRP can also be used in conjunction with total joint replacement, gastric bypass, and bone grafting procedures.

With the second buoy 22 in the first position, the second valve 67 defined by the second aperture 36 in the guide post 18 is opened. As illustrated in FIG. 6, continued pressure exerted by the plunger 16 causes the PPP between the second buoy 22 and the plunger base 24 to pass through the second aperture 36. The PPP moves through the second aperture 36, the channel 32, and the flexible tube 70 to the port 14. From the port 14 the PPP is expelled from the device 10 through any suitable applicator attached to the port 14 and applied to a desired area.

PPP can be used for a variety of suitable purposes, such as to facilitate wound closure. PPP can also be used as a fibrin sealant, a fibrin glue, and for facial reconstruction.

RBCs are typically not extracted from the separation device 10. However, one skilled in the art will appreciate that the device 10 can be provided with a third valve between the port 14 and the first buoy 20 through which the RBCs may be withdrawn from the device 10.

Thus, the device 10 provides an all-in-one blood separation device. The device 10 can be introduced into a sterile field in a sterile package. After the device 10 is in the sterile field and removed from the sterile package, the device 10 can be used by sterile personnel as described above to draw blood directly from a source, such as a patient's blood vessel, separate the RBC, PPP, and PRP blood fractions during centrifugation, and deliver the fractions directly to a wound site to facilitate healing. The device 10 eliminates the need for separate syringes, or other devices, to draw the whole blood from the patient, transfer the drawn blood into a device suitable for centrifugation, and apply the separated blood fractions to a wound site. Therefore, the device 10 also eliminates any possibility of the blood being contaminated during transfer between different syringes or devices or from sterile to non-sterile fields.

The device 10 can also be used to separate components of bone marrow aspirate. For example, bone marrow aspirate can be obtained using any suitable bone marrow aspiration device, such as that described in U.S. patent application Ser. No. 12/210,372 titled Bone Marrow Aspiration Needle, filed on Sep. 15, 2008 and assigned to Biomet Biologics, LLC, which is hereby incorporated by reference. In particular, the device 10 can be attached directly to the inner aspiration needle described in U.S. patent application Ser. No. 12/210,372 through cooperation between the Luer lock 15 and the Luer lock of the inner aspiration needle.

To obtain bone marrow aspirate for separation, the bone marrow aspiration device, including the inner aspiration needle, is advanced into the bone cortex and ultimately into the bone marrow cavity from which the bone marrow aspirate is withdrawn. The bone marrow aspirate is drawn into the device 10 in the same manner that whole blood is, as described above. Any suitable amount of bone marrow aspirate can be used, such as about 300 cc, about 60 cc, or less than 60 cc. A suitable anticoagulant in a suitable amount is added to the bone marrow aspirate after it has been withdrawn from the bone marrow cavity.

The device 10 is centrifuged in the same manner as described above with respect to the separation of whole blood. Centrifugation causes the bone marrow aspirate to separate such that bone marrow plasma is isolated between the second buoy 22 and the plunger base 24. The heavy components of the bone marrow aspirate, such as the RBCs, are isolated between the first buoy 20 and the port 14. The multipotent cells are isolated between the first buoy 20 and the second buoy 22 in the gap formed between the first and the second buoys 20 and 22 when the second buoy 22 is in the second position. The multipotent cells and the bone marrow plasma can be removed from the device 10 in the same manner described above with respect to PRP and PPP.

When using the device 10 to isolate multipotent cells from bone marrow aspirate the first buoy 20 is provided with a greater density than the second buoy 22. The density of the first buoy 20 and the density of the second buoy 22 when the device 10 is used to separate components of bone marrow aspirate is generally the same as the density of the buoys 20 and 22 when the device 10 is used to separate whole blood.

The device 10 can be used to isolate most any liquid composition into its constituent components by density. In order to adapt the device 10 to separate different components, the density of the first buoy 20 and the second buoy 22 can be modified to approximate the density of the particular components to be isolated. As a result, the first and the second components to be isolated will be separated by the second buoy 22 with the first component isolated between the first buoy 20 and the second buoy 22 and the second component isolated between the second buoy 22 and the plunger base 24.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A device having a separation chamber for separating components of a composition according to density comprising:
 a port that provides fluid communication between an interior and an exterior of said separation chamber;
 a buoy guide post;
 a first buoy fixedly mounted to said buoy guide post and slidably mounted within said separation chamber;
 a second buoy slidably mounted to said buoy guide post and movable between a first position and a second position along said buoy guide post;
 a passage defined in said buoy guide post that is in fluid communication with said port;
 a first valve in said buoy guide post in fluid communication with said passage and an area of said separation chamber between said first buoy and said second buoy;
 a second valve in said buoy guide post in fluid communication with said passage and an area of said separation chamber between said second buoy and an end of said separation chamber that is opposite to said port;
 wherein said second buoy closes said first valve and opens said second valve when in said first position; and
 wherein said second buoy opens said first valve and closes said second valve when in said second position; and
 wherein said second buoy has a density such that after spinning said device for a suitable period of time a first component of said composition is isolated between said first buoy and said second buoy and a second component of said composition is isolated between said second buoy and said end of said separation chamber that is opposite to said port.

2. The device of claim 1, further comprising a plunger that is slidably movable within said separation chamber, said plunger includes a plunger base that is removably attached to a plunger handle.

3. The device of claim 2, further comprising a plunger stop that restricts movement of said plunger.

4. The device of claim 1, wherein said first buoy has a density of between about 1.070 g/ml and about 1.095 g/ml.

5. The device of claim 1, wherein said first buoy has a greater density than said second buoy.

6. The device of claim 1, wherein said second buoy has a density of between about 0.93 g/ml and about 0.955 g/ml.

7. The device of claim 1, wherein said first buoy has a top surface that faces said second buoy, said top surface is concave; and
 wherein said first buoy has a bottom surface that is opposite to said top surface, said bottom surface is convex.

8. The device of claim 1, wherein said device includes a syringe.

9. The device of claim 8, wherein said syringe is connected to said port with an extension nozzle.

10. The device of claim 8, wherein said syringe is connected directly to said port.

11. The device of claim 1, wherein said device is configured to separate components of any of the following compositions: whole blood, blood plasma, mononuclear cells, bone marrow aspirate, spinal fluid, and fat.

12. The device of claim 1, wherein said first and said second buoys are of a density configured to isolate the following: platelet rich plasma between said first buoy and said second buoy; red blood cells on a side of said first buoy that is opposite to said second buoy; and platelet poor plasma on a side of said second buoy that is opposite to said first buoy.

13. The device of claim 1, wherein said first and said second buoys are of a density configured to isolate the following: multipotent cells between the first buoy and the second buoy; red blood cells on a side of said first buoy that is opposite to said second buoy, and bone marrow plasma on a side of said second buoy that is opposite to said first buoy.

14. The device of claim 1, further comprising a flexible conduit that connects said passage of the buoy guide post to said port.

15. The device of claim 1, further comprising a polymeric ring that extends around a cylindrical sidewall of said second buoy.

16. The device of claim 1, further comprising a first polymeric ring and a second polymeric ring that each extend around an outer diameter of said buoy guide post, said first polymeric ring and said second polymeric ring are positioned on opposite sides of said second valve.

17. A device having a separation chamber for separating components of a composition according to density comprising:
   a port that provides fluid communication of the composition from an exterior of said chamber to an interior of said chamber;
   a first buoy slidably mounted within said separation chamber; and
   a second buoy slidably mounted within said separation chamber;
   wherein said second buoy has a density such that after spinning said device for a suitable period of time a first component of said composition is isolated between said first buoy and said second buoy and a second component of said composition is isolated between said second buoy and an end of said separation chamber that is opposite to said port;
   wherein said port provides fluid communication of both said first component and said second component from said interior of said chamber to said exterior of said chamber;
   a buoy guide post extending along a longitudinal axis of said separation chamber in fluid communication with said port;
   wherein said first buoy and said second buoy are each slidably mounted to the buoy guide post;
   a first valve in the buoy guide post;
   a second valve in the buoy guide post; and
   wherein said second buoy closes the first valve in the buoy guide post and opens the second valve in the buoy guide post when in a first position, said second buoy opens said first valve and closes said second valve when in a second position different from the first position.

18. The device of claim 17, wherein said first buoy is connected to said second buoy.

19. The device of claim 17, wherein said first buoy is not connected to said second buoy.

20. A device for separating components of a composition according to density comprising:
   a separation chamber;
   a buoy guide post within said separation chamber;
   a first buoy mounted to said buoy guide post;
   a second buoy mounted to said buoy guide post;
   a passage defined in said buoy guide post that is in fluid communication with an exterior of said separation chamber;
   a first valve in said buoy guide post; and
   a second valve in said buoy guide post;
   wherein:
      said second buoy closes said first valve and opens said second valve when in a first position;
      said second buoy opens said first valve and closes said second valve when in a second position different from the first position; and
      said second buoy has a density configured such that after spinning said device for a suitable period of time a first component of said composition is isolated between said first buoy and said second buoy, and a second component of said composition is isolated between said second buoy and an end of said separation chamber.

* * * * *